(12) United States Patent
Lachenbruch

(10) Patent No.: US 7,727,267 B2
(45) Date of Patent: *Jun. 1, 2010

(54) SELF-POWERED STEADY-STATE SKIN-COOLING SUPPORT SURFACES

(76) Inventor: Charles Arthur Lachenbruch, 126 Linwood La., Summerville, SC (US) 29483

( * ) Notice: Subject to any disclaimer, the term of this patent is extended or adjusted under 35 U.S.C. 154(b) by 1205 days.

This patent is subject to a terminal disclaimer.

(21) Appl. No.: 11/301,216

(22) Filed: Dec. 12, 2005

(65) Prior Publication Data

US 2007/0135878 A1 Jun. 14, 2007

(51) Int. Cl.
*A61F 7/00* (2006.01)

(52) U.S. Cl. .................. 607/108; 607/98; 607/112; 607/114

(58) Field of Classification Search .......... 607/96, 607/108, 112, 114
See application file for complete search history.

(56) References Cited

U.S. PATENT DOCUMENTS 6,145,143 A 11/2000 Hicks et al.
6,497,720 B1* 12/2002 Augustine et al. ............. 607/96
6,699,266 B2* 3/2004 Lachenbruch et al. ......... 607/96
6,772,825 B2* 8/2004 Lachenbruch et al. ......... 165/46
7,273,490 B2* 9/2007 Lachenbruch ............... 607/104
2003/0046762 A1 3/2003 Stolpmann

FOREIGN PATENT DOCUMENTS

DE 195 14295 A1 10/1996
EP 0 621 026 A2 3/1994

* cited by examiner

*Primary Examiner*—Roy D Gibson
*Assistant Examiner*—Kaitlyn E Helling
(74) *Attorney, Agent, or Firm*—B. Craig Killough

(57) ABSTRACT

A refrigerant-containing bladder or container is positioned underneath the body. Heat absorbed from the body vaporizes the refrigerant, which expands to cooler remote regions of the bladder. Heat is then withdrawn from the edges of the container by thermally conductive pathways that distribute heat from this container to a cooler area that is not underneath the body. The cooled refrigerant condenses, and is returned to the regions of the device that are under or adjacent to the central and warmest parts of the body. The heavier and warmer portions of the body force the bladder to the lowest point. Alternatively, heat is transferred from the body via a specific highly thermally conductive layer or layers of material(s) that is (are) soft, pliable, and comfortable to sit or lie on. This layer joins conductive materials that are configured to transport heat and diffuse it to the cooler environment.

20 Claims, 26 Drawing Sheets

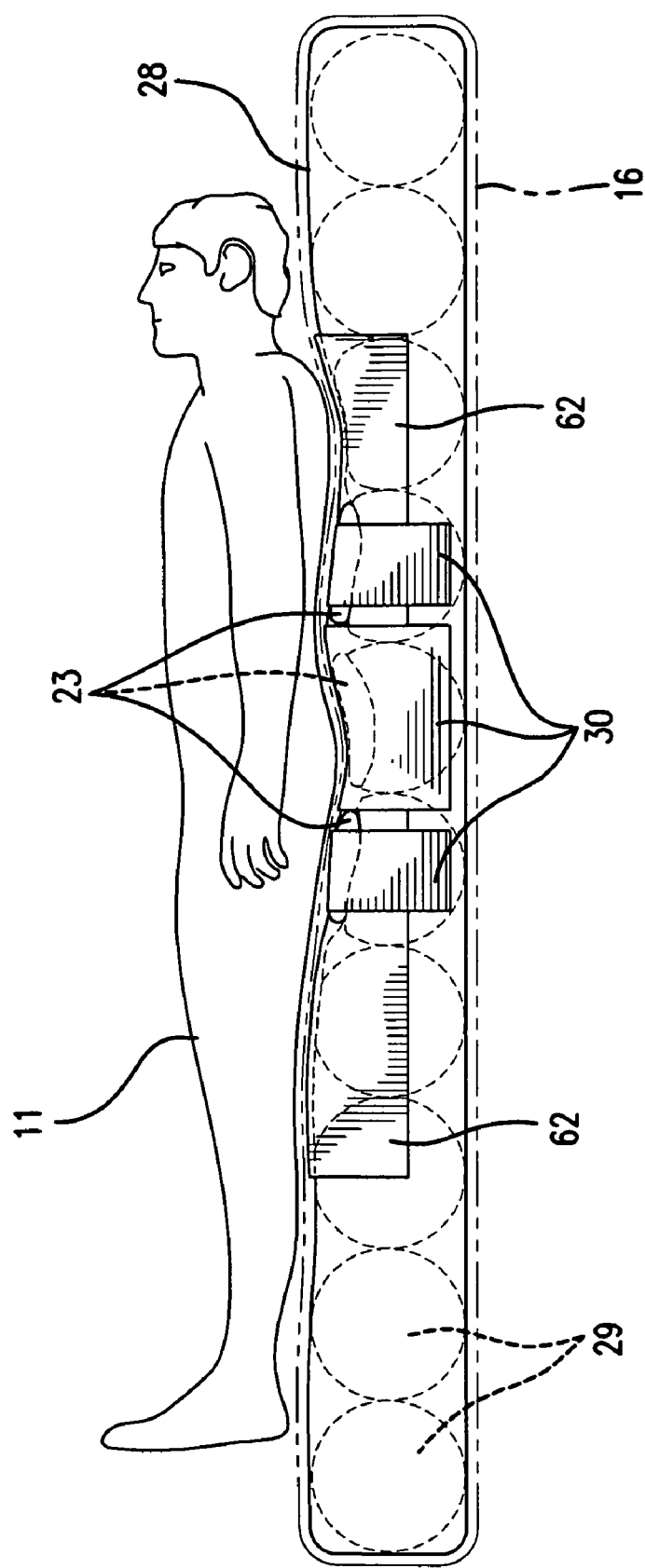

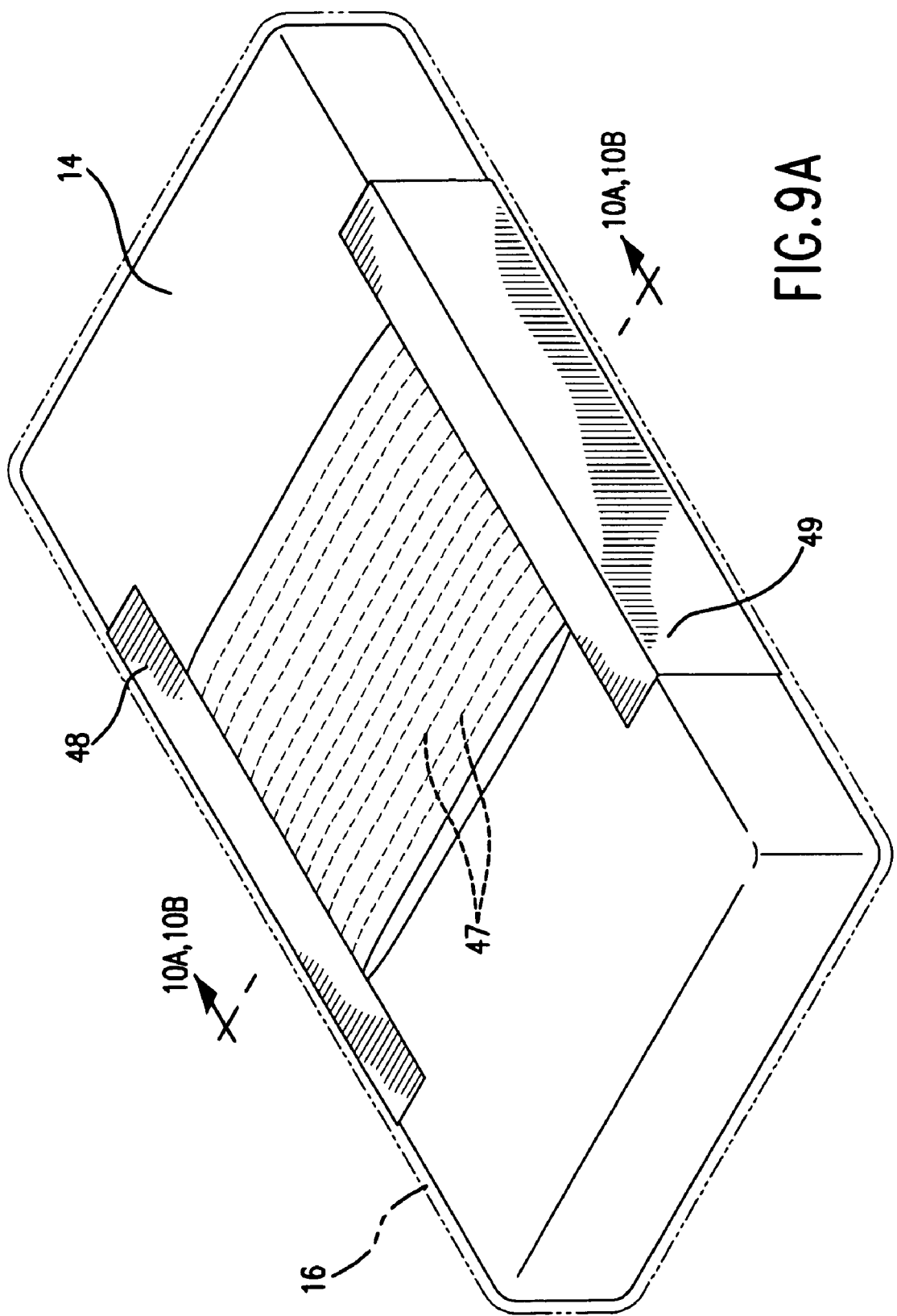

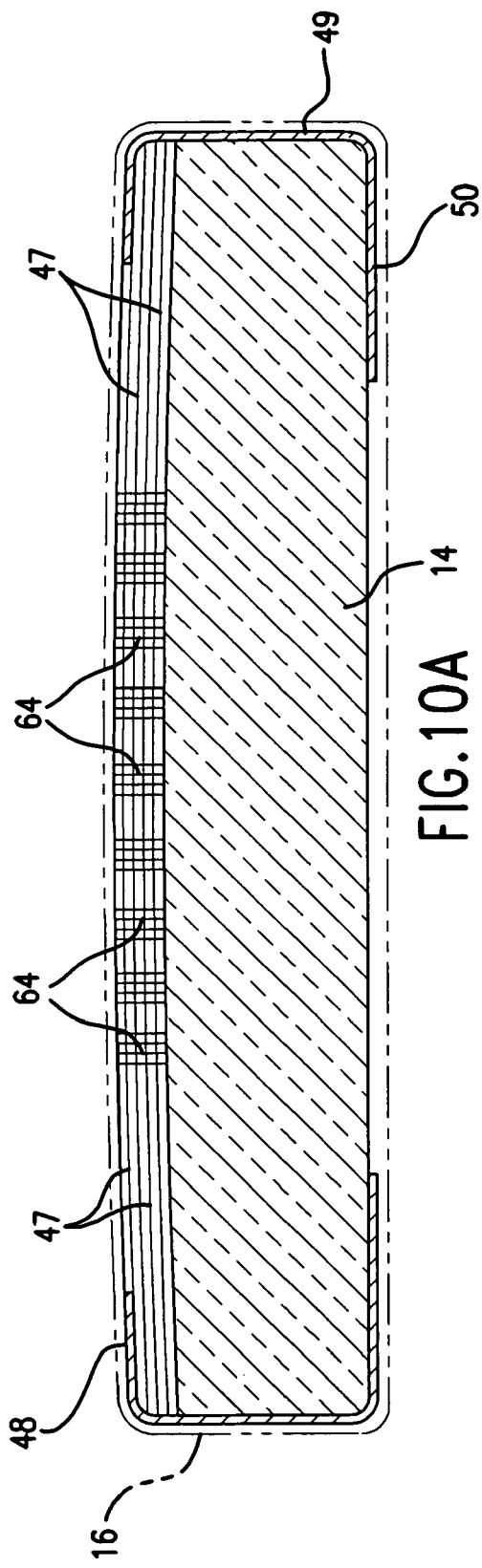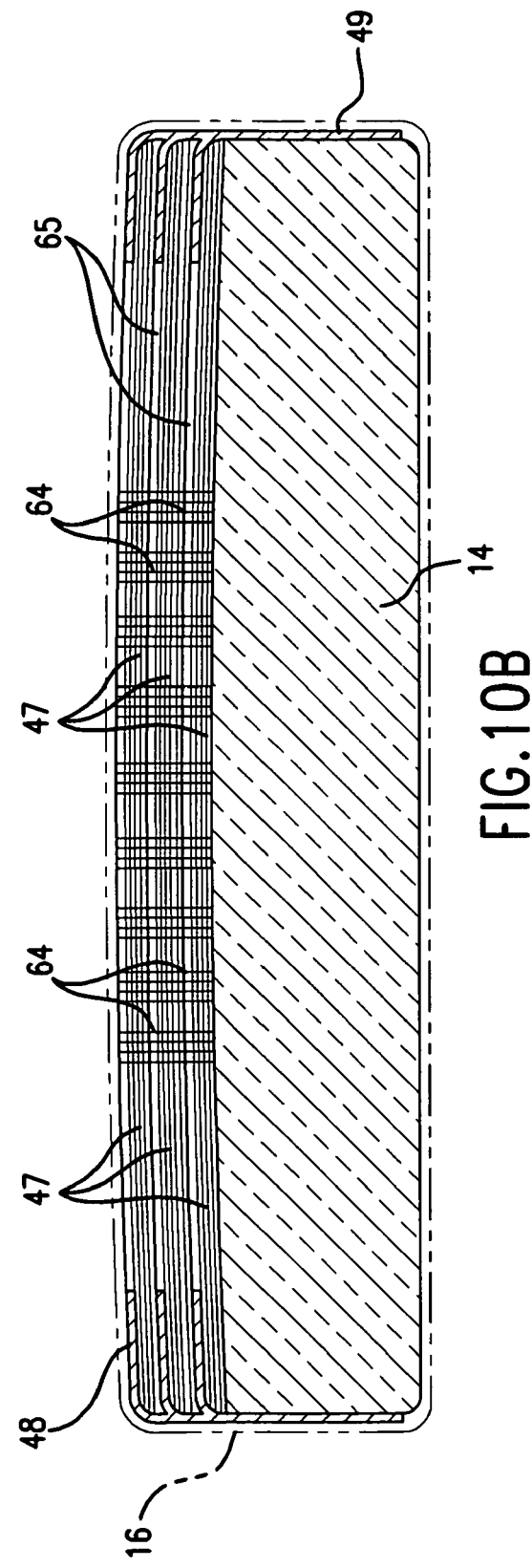

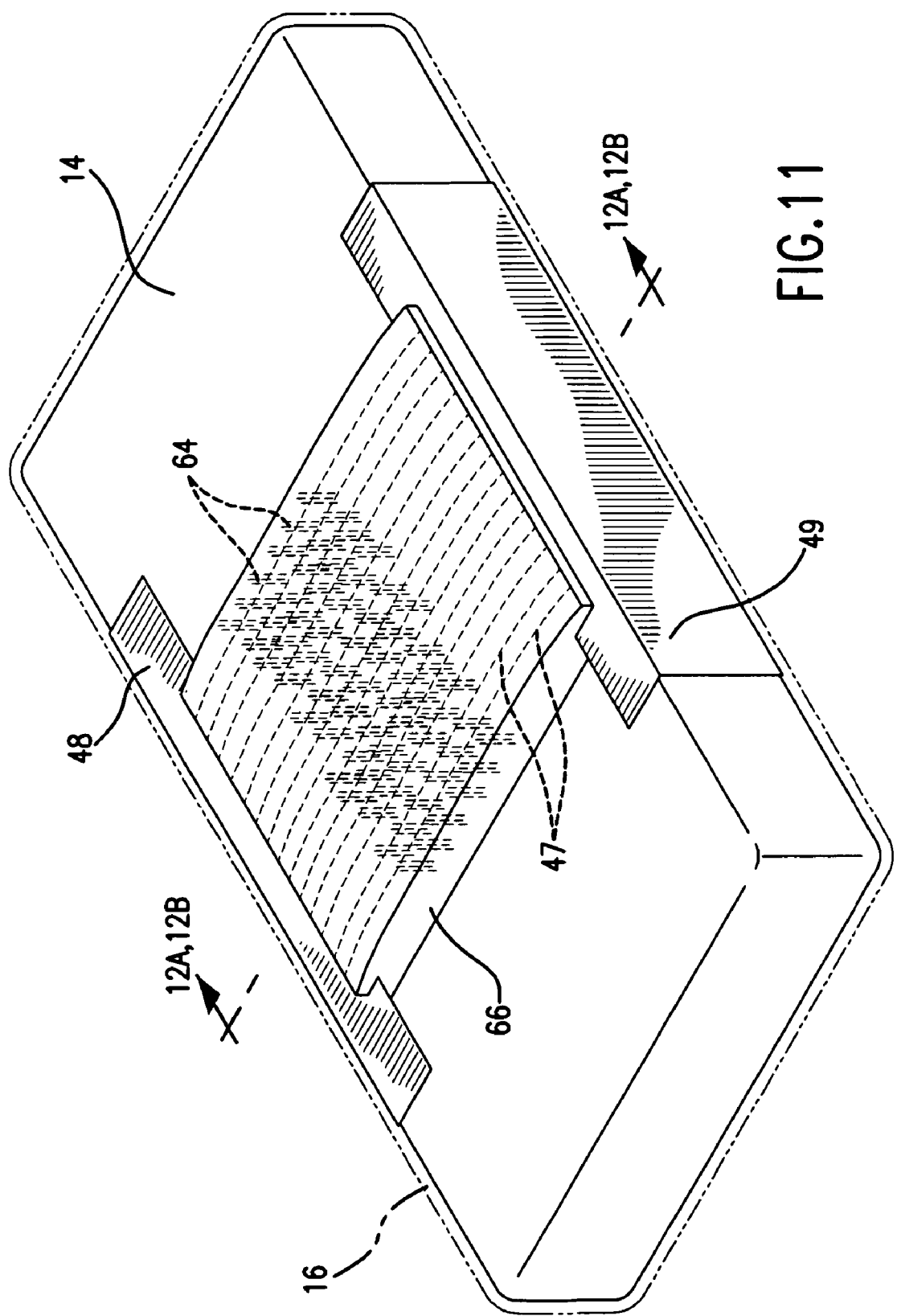

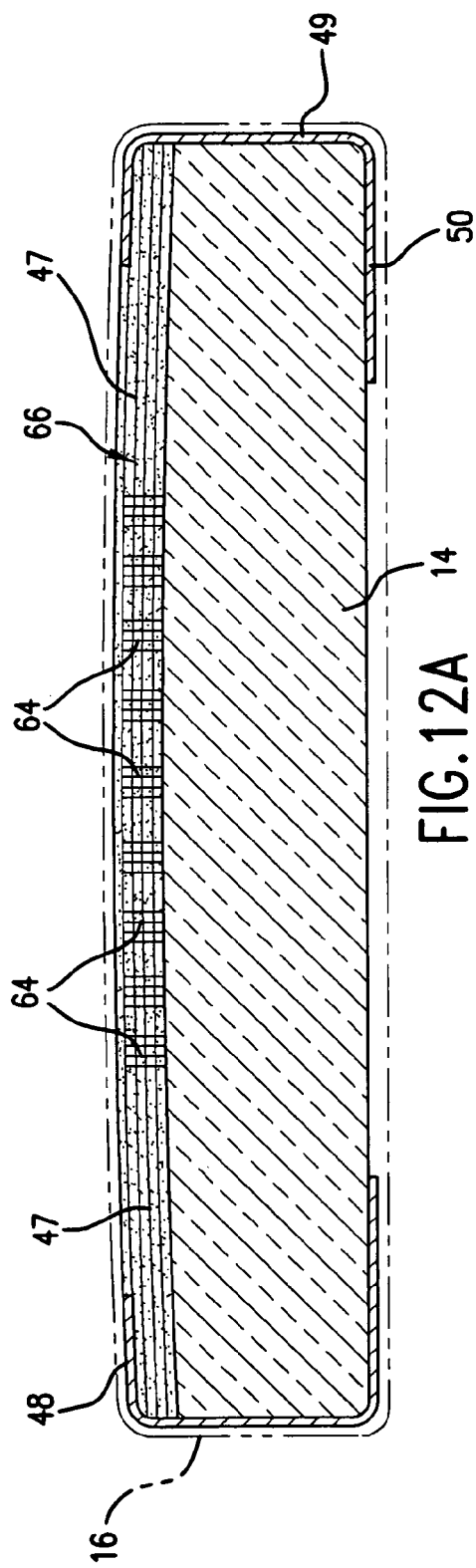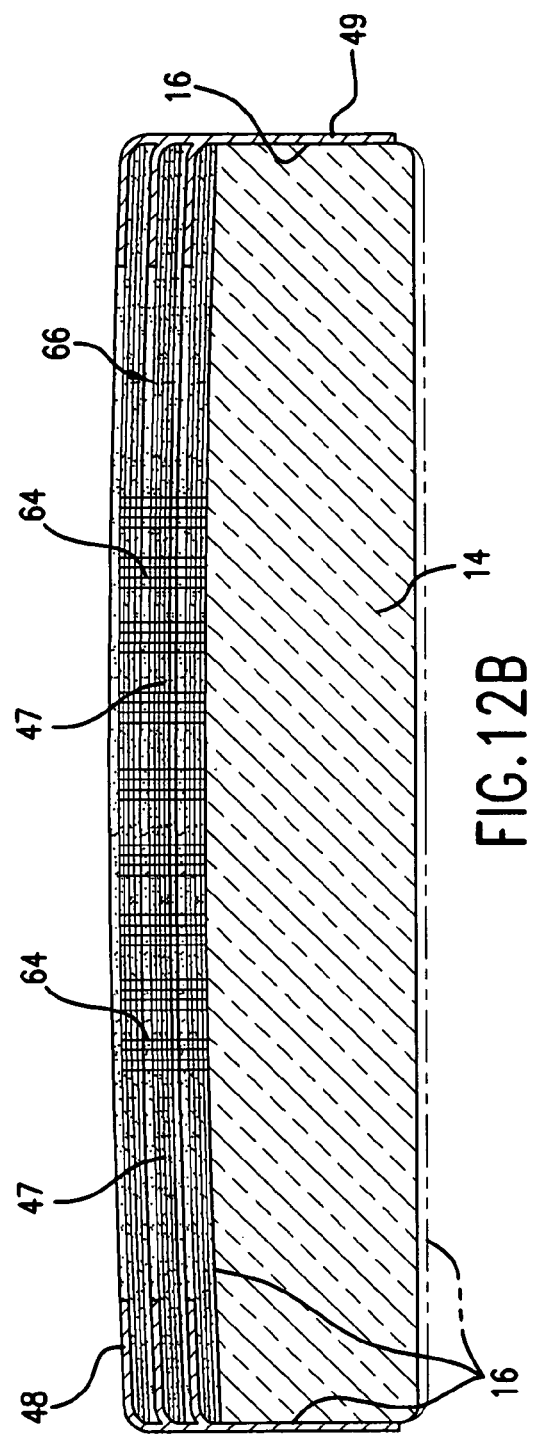

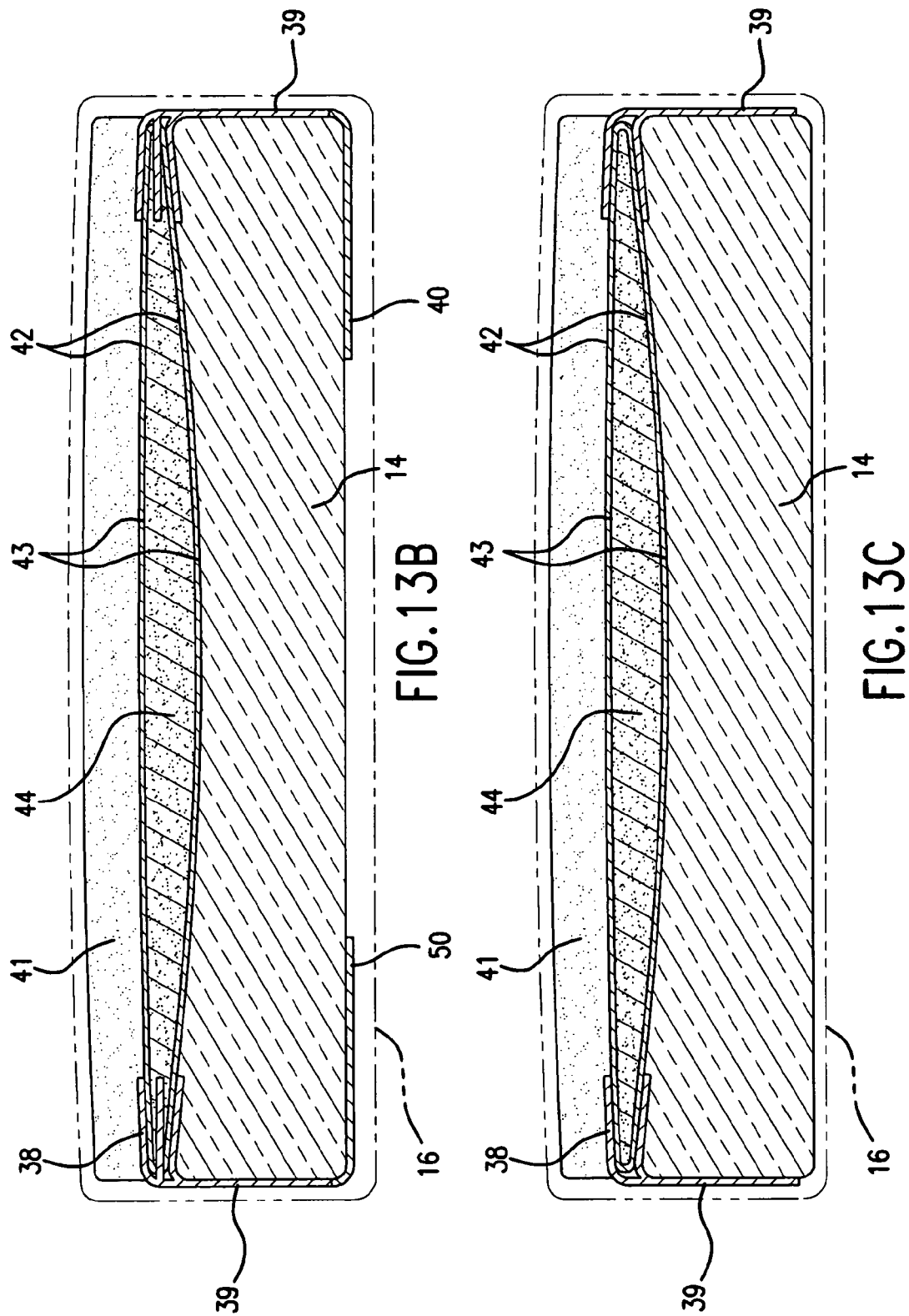

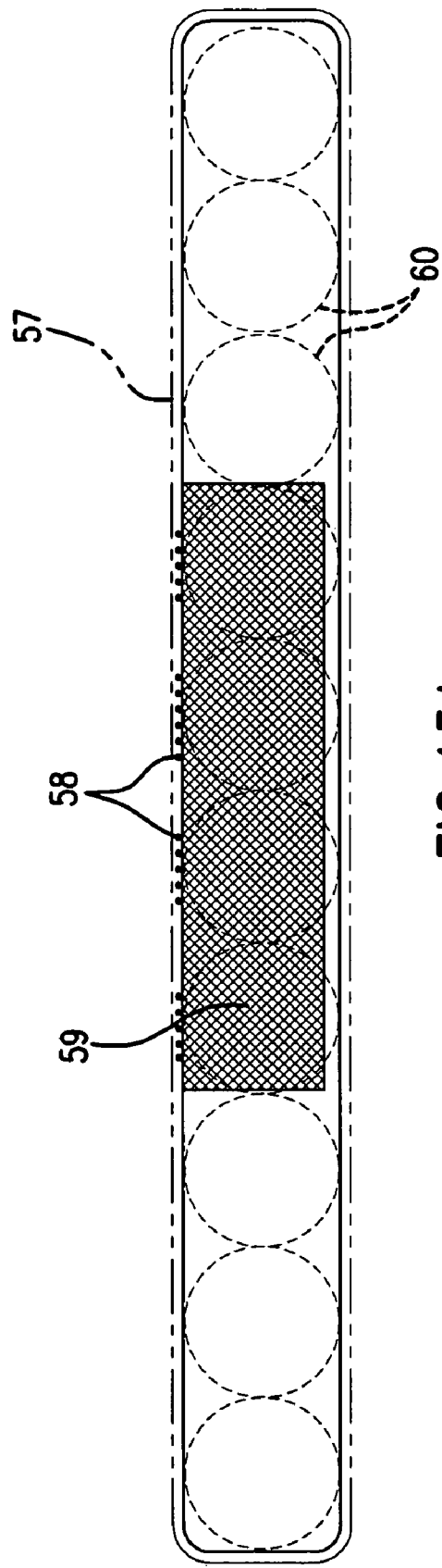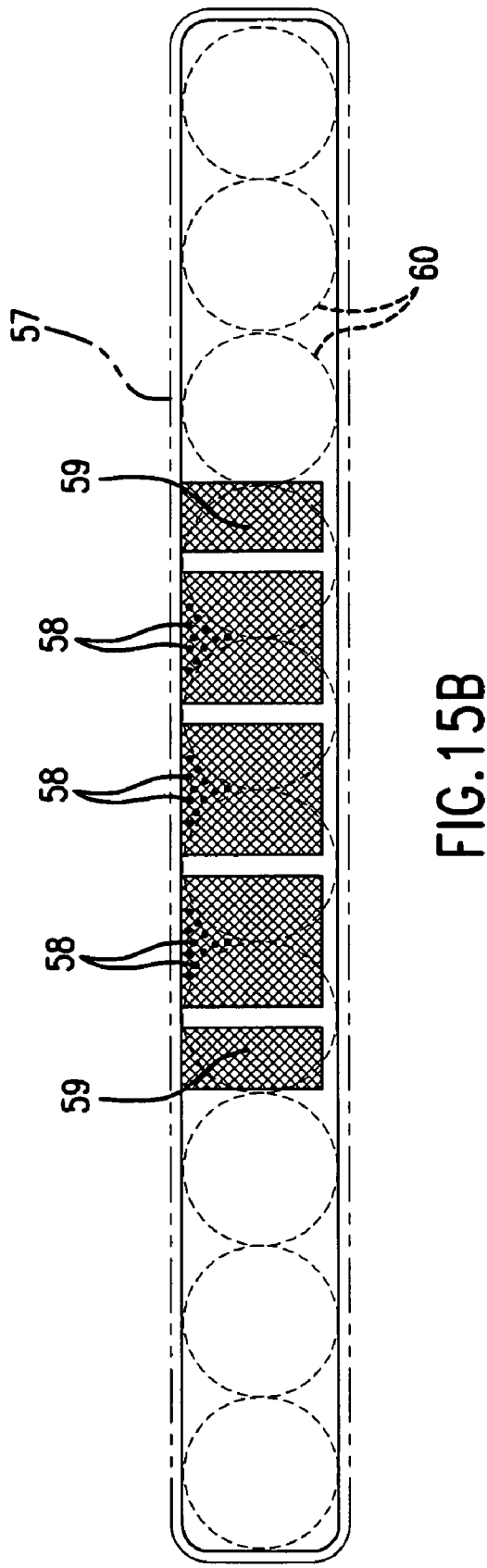

SELF-POWERED STEADY-STATE SKIN-COOLING SUPPORT SURFACES

Applicant claims the benefit of Ser. No. PCT/US2004/003628 filed Feb. 10, 2004.

FIELD OF THE INVENTION

The present invention relates to cooling support surfaces, and is more directly related to a non-powered or self-powered skin-cooling support surface configured to absorb and transport heat from a user to a cooler environment

BACKGROUND OF THE INVENTION

Bedsores, or decubitus ulcers, can be a serious problem in bedridden or wheelchair-bound patients, particularly for people who are paralyzed, emaciated, post-surgical, elderly, or diabetic. The ulcers frequently penetrate through not only the skin, but the underlying muscle and bone as well. With the serious infections that often ensue, pressure ulcers can become life-threatening.

As the elderly population increases with demographic trends, the incidence is likely to increase. The results of the last National Pressure Ulcer Surveys from 1989 to 1997 indicate that despite the growth in the wound care and therapeutic surface industries, the incidence of pressure ulcers appears to have increased over this period. It is clear that while new treatment solutions may be relatively effective, their cost precludes their use by the vast majority of caregivers in the settings in which pressure ulcers and other chronic wounds must be managed. Disproportionately, this includes the nursing home, home care, and of course, the overseas markets where resources are limited. The consensus among thought leaders in the international medical community supports the contention that less expensive medical solutions are required generally and urgently. The invention to be described here is intended to fulfill this societal need.

Bedsores, or pressure ulcers, were named because they most commonly develop where tissue pressures are greatest—over the bony prominences, such as the heels, sacrum (tailbone), ischia, greater trochanters, and ankles (external malleoli). At these sites where the pressure on the skin is concentrated, blood flow can be restricted. If nutrient deficit exceeds tissue demand over a given interval, the tissue will start to die locally, resulting in an ulcer.

It is generally recognized that it is important to limit both skin warming and moisture accumulation to effectively combat skin breakdown. This has been embraced by professional bodies and recognized thought-leaders in the wound care medical community.

The normal core temperature of the human body is between 36° and 38° C. Skin temperature typically ranges between about 30° C. and about 34° C., depending on ambient temperature, the amount and type of clothing being worn, the core temperature, and where the skin is located on the body. However, on a typical mattress, seat cushion, seat back, etc., heat is trapped between the body and the covered skin surface, and the skin temperature rises rapidly to and may reach 35 to 37 degrees C. This small temperature elevation that occurs with the skin in contact with the mattress, seat cushion, etc., has important physiologic effects.

When a patch of skin is warmed beyond a specific level referred to as the "perspiration threshold" of approximately 32 to 34° C., local perspiration in the region increases markedly. The accompanying moisture softens the skin (maceration), which makes it more susceptible to breakdown. The build-up of moisture increases the friction between the skin and the surface materials resulting in increased shear stresses in the tissue. It has also been shown that elevated skin temperature is associated with increased metabolic demand, therefore, researchers have speculated that elevated skin temperature increases the susceptibility of the tissue to ischemic injury, particularly when both nutrient supply and metabolite removal are reduced by loading. Generally, tissue metabolic rates increase by approximately 10% for each one degree Celsius increase in temperature. Warmed tissue generates an increased demand for blood supply that can be met when the skin is not under significant load. At interface pressures of 20 or more mm Hg, as occur under the bony prominences on a mattress or seat, blood flow can not be increased to meet this demand, and the tissue becomes ischemic. Other research looked directly at tissue injury and temperature. One demonstrated that skin tissue with reduced blood supply has been shown to be less susceptible to injury when tissue temperatures were slightly reduced. In a second study, identical pressures were applied to the skin tissue of research animals at nearly 300 sites. The skin temperatures at the interface varied between 28 and 36 degrees C. The results showed a very strong positive correlation—nearly perfect, in fact—between skin temperature and degree of skin breakdown.

When skin temperatures are maintained within certain limits, the person or animal is more comfortable. For humans, comfort is optimal when the skin temperature is maintained close to its natural (non or lightly insulated) temperature of 30 to 34 degrees C., even when insulated support conditions are employed. The devices described herein have important medical and non-medical applications. The non-medical applications include most seating and bedding applications such as mattresses for the home, seating or seat backs for the office, home, and vehicle markets.

Steady State vs. Temporary Cooling

Limiting the warming of the skin that occurs when it is insulated during therapeutic support reduces the risk of bedsores, aids healing, and enhances comfort. In the prior art, skin cooling is accomplished using what is known as a "low-air-loss bed" (LAL), which may cost $40,000.00 or more. LAL beds utilize pumps or blowers to eject steady streams of air through small vents in the bladders of an air mattress. Air flowing across an underside of the ticking convectively removes heat that passes from the patient's body into the surface. Heat from the body is subsequently transported with the ejected air from the bed as it is continually cycled. Although some LAL surfaces are effective at providing steady state cooling, they require power that is typically provided by electro-mechanical means, such as motors. Accordingly, LAL surfaces may be noisy, require extensive engineering and operator training, and they may be imposing to both patient and caregiver. Additionally, they may increase the risk of bio-aerosol contamination, i.e., the risk of spreading germs in the hospital or nursing home environment.

Temporary skin cooling can be accomplished by increasing the heat input required to increase the temperature of the surface. The quantity of heat required to increase a temperature of a specific quantity of material by a specific temperature is called the specific heat. For example, the specific heat of a specific alloy of aluminum can be expressed in Joules/kg-degree K. The quantity of heat required to raise the temperature of a given body is referred to as the heat capacity of the body. If a large body and a small body are both made of the same material, for example, the larger body will have a greater heat capacity although both will have the same specific heat. A surface of high specific heat material such as silicone gel or fluid, or even a waterbed, will provide temporary cooling, because a great deal of the body's heat will flow from the skin, initially at approximately 30 to 34° C. to the surface, initially at 23° C. room temperature. Phase change material which, as it undergoes phase-change, tremendously increases the capacity of a material to absorb heat, while maintaining the same temperature. All such surfaces will initially feel quite cool to the user. Such approaches, however, only delay skin warming. A steady flux of heat into the surface will eventually cause all of the phase change material to change phase, and/or the high heat capacity material to warm. In order to provide continuous, steady-state cooling, the heat must be removed from the system and transferred to the environment or to another system that is external to the surface to be cooled. A need exists for non-powered, or, stated otherwise, self-powered devices to provide steady state cooling at the level of the expensive, externally powered LAL surfaces currently in use. It is particularly valuable to develop such a device that provides cooling without spreading airborne pathogens from the occupant's skin surface into the common environment.

It is important to note that materials of sufficiently high thermal conductivity, mechanical compliance, and relatively low cost did not exist for such an application until the last few years. Heat transfer by conduction has not generally been considered practical for use in applications in which heat transfer paths are large (greater than 10 cm) and temperature differences are small (less than 10° C.) between the region to be cooled and the environment. This is particularly true for biomedical applications.

The likelihood of bedsore formation is reduced by lowering tissue metabolic rate (and therefore reducing tissue ischemia in pressurized tissue with reduced blood flow) and limiting local perspiration, which weakens the outer skin layer (the stratum corneum) over time. These inventions may be used as an aid in the healing of early stage bedsores or other skin ulcers. Moderate cooling of the skin during support (from 35° C. to 37° C. down to the 30° C. to 34° C. range) also makes the user more comfortable. The proposed inventions, therefore, have not only medical applications, but applications in the general consumer niche as well.

SUMMARY OF THE INVENTION

Two embodiments of the invention are presented. The first embodiment is broadly referred to as Gas Expansion Devices, and the second group is broadly referred to as Conductive Devices.

In the Gas Expansion Devices, a refrigerant-containing bladder or container is positioned underneath the body. Heat absorbed from the body vaporizes the refrigerant, which expands to the cooler remote regions of the bladder, which are typically at the edges of the support surface. Heat is then withdrawn from the edges of the container by thermally conductive pathways that distribute heat from this container to a cooler area that is not underneath the body. The cooled refrigerant then condenses, and is returned to the regions of the device that are under or adjacent to the central and warmest parts of the body. The portions of the body that produce the most heat are typically the heaviest portions of the body. The heavier and warmer portions of the body force the bladder to the lowest point. In sequence, the refrigerant, therefore, is transported away from the warm, central region of the body (buttocks and lower torso) initially by the gas expansion that accompanies phase change, and then back to this region by gravity.

In the Conductive Devices, heat is transferred from the body via a specific highly thermally conductive layer or layers of material(s) that is (are) soft, pliable, and comfortable to sit or lie on. This layer joins conductive materials that are configured to transport heat and diffuse it to the cooler environment at a lower cost than the conductive material used in the cooling support region.

DESCRIPTION OF THE DRAWINGS

A more complete understanding of the invention and its advantages will be apparent from the following detailed description taken in conjunction with the accompanying drawings, wherein examples of the invention are shown, and wherein:

FIGS. 9 through 16 withdraw heat primarily via conduction (Conduction Devices). It should be noted, of course, that both methods of heat transfer obviously occur to some minor degree in both systems and various aspects of each class of surfaces could be combined in some designs.

Figure 1A:
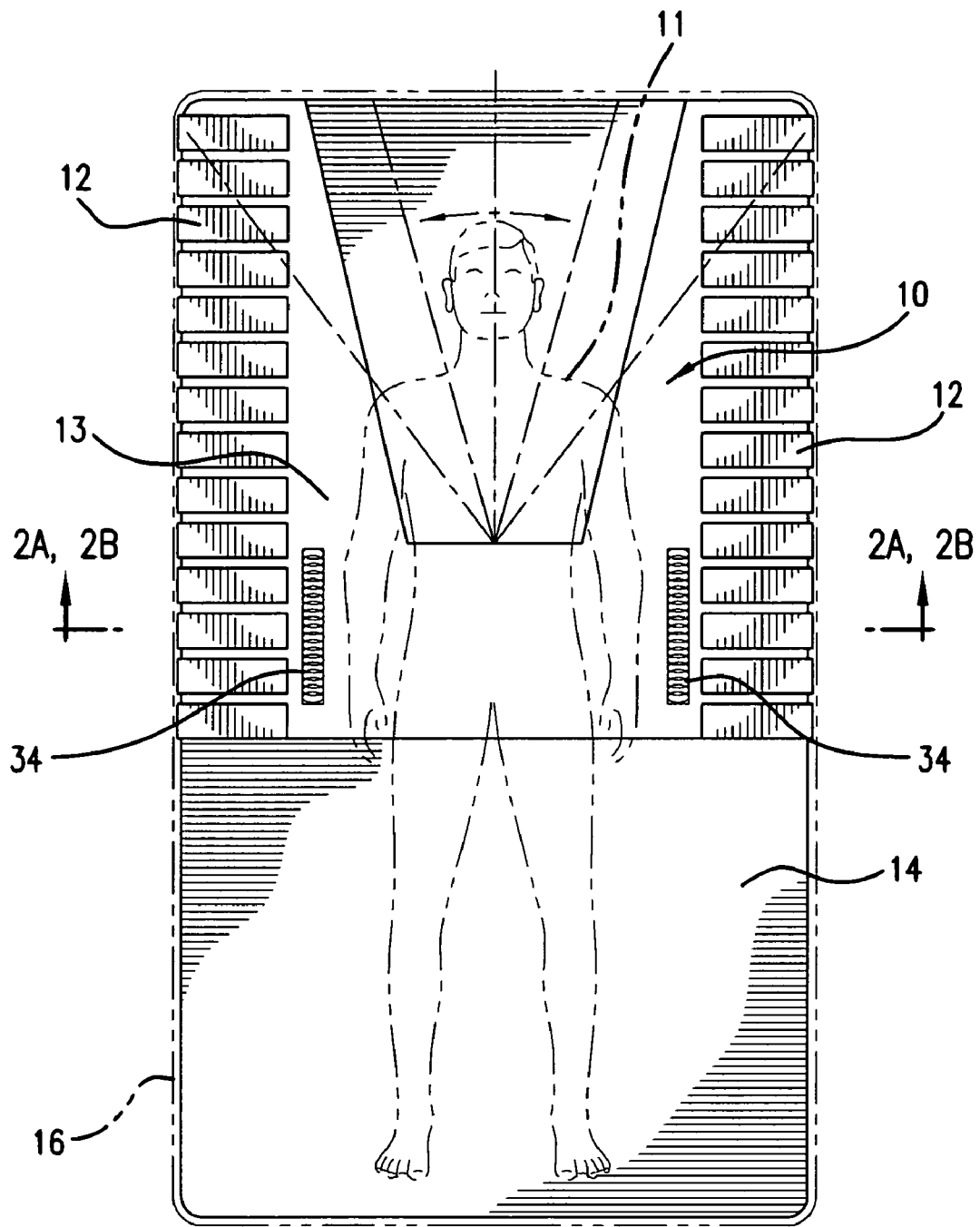
FIG. 1A shows a top view of a therapeutic support surface pad according to the present invention, shown in use by a person on a mattress; the radiating dashed lines indicate possible bladder shapes. Note that FIGS. 1 through 8 depict various embodiments of cooling surfaces that transfer heat from the body primarily according to liquid to gas phase change and gas expansion (Gas Expansion Devices).
Figure 1B:
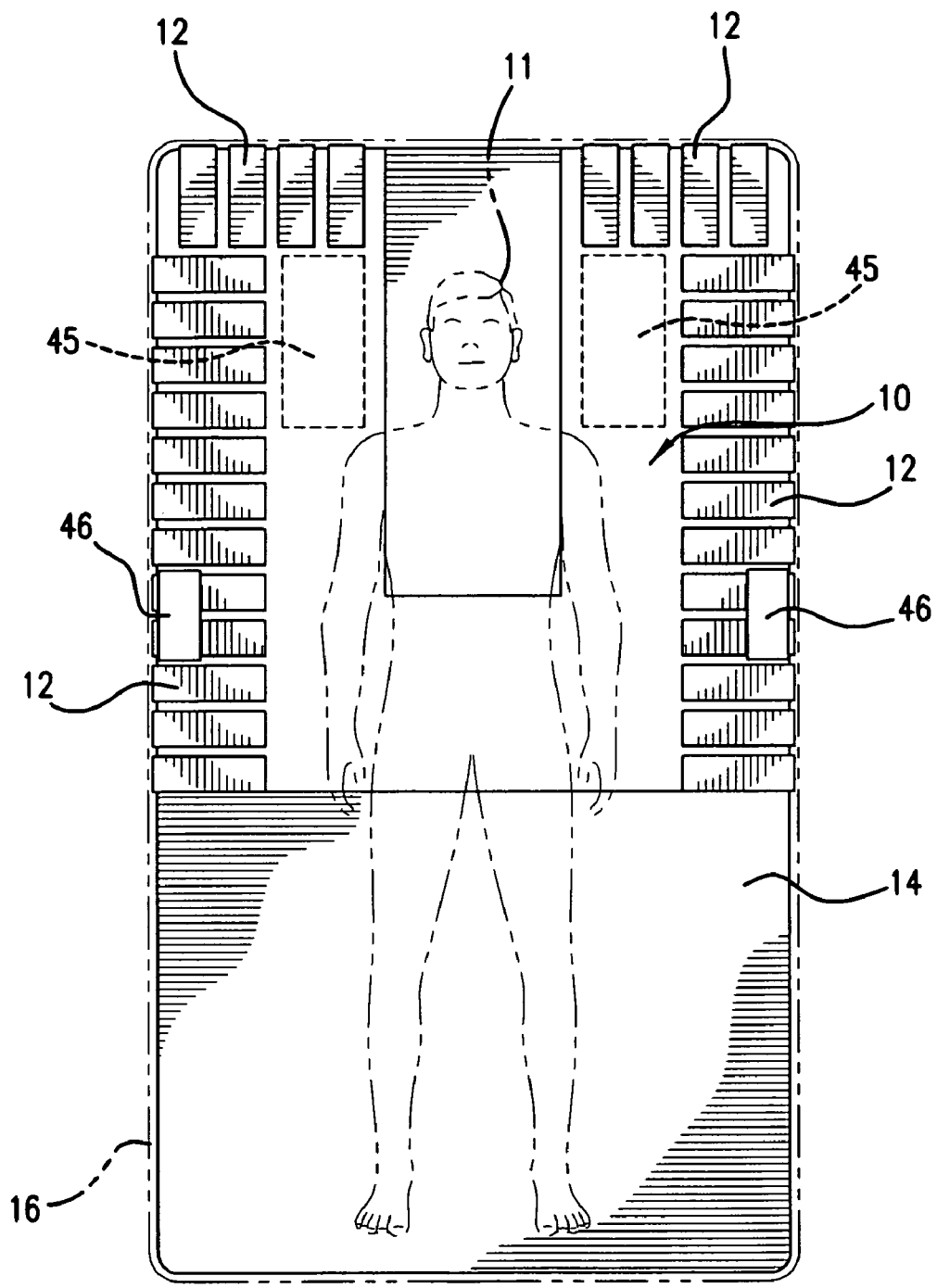
FIG. 1B shows a top view of a second embodiment of a therapeutic support; surface in use. This shows a different configuration of the bladder. It should be noted that the conduction strips extend not only over the sides of the mattress but extend over the top as well. The length, width, and material properties of these strips are dependent upon a number of heat transfer factors (ambient temperature, occupant size and need for cooling, etc.).
Figure 1C:
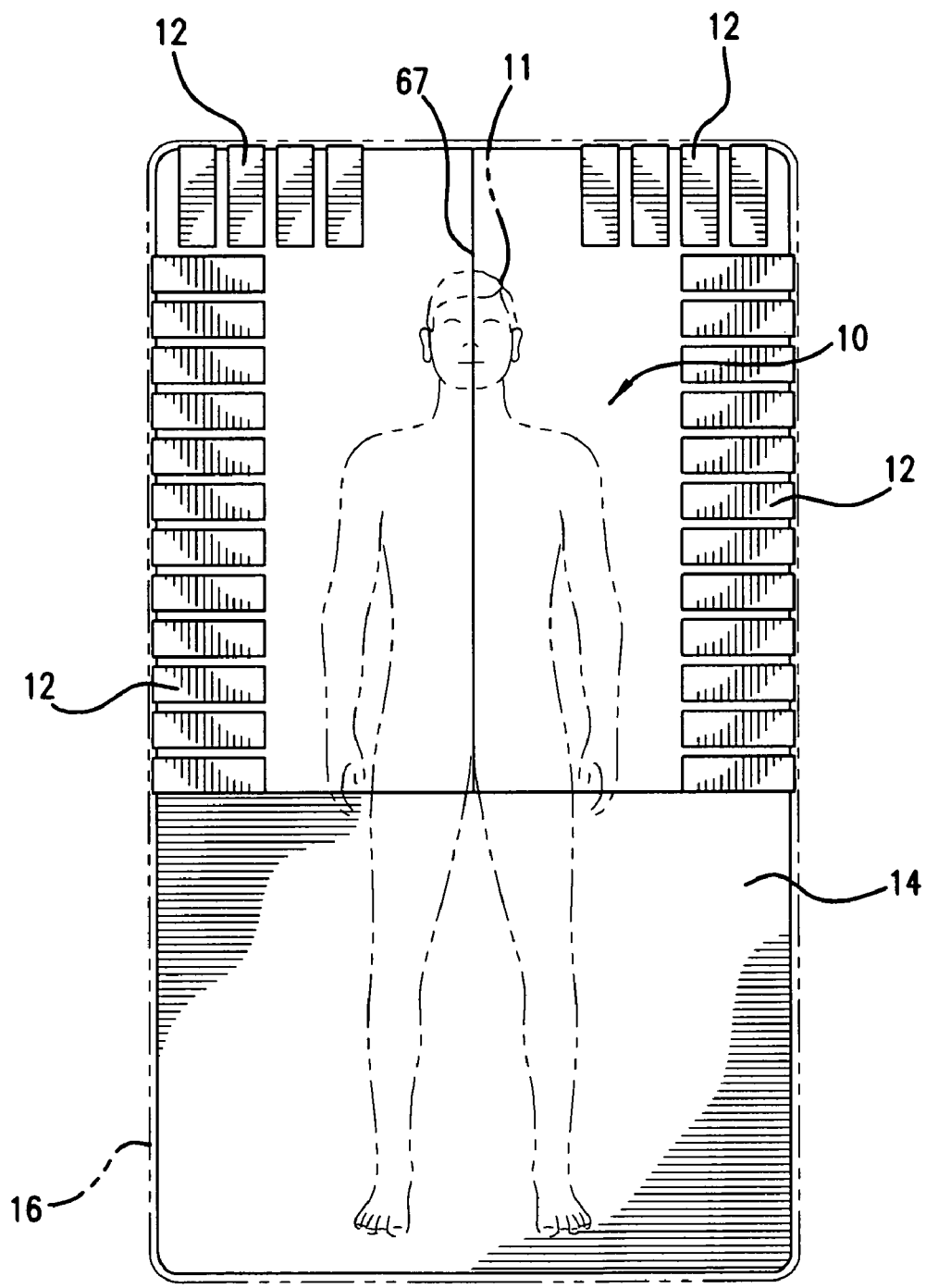
FIG. 1C shows a top view of a third embodiment of a therapeutic support surface in use. A pair of bladders is joined along the center line. Note that for ease of construction any of these bladder shapes shown in FIGS. 1 through 8 may be manufactured by joining two bladders, such as by joining along a seam through which there is no flow of refrigerant between sections.
Figure 1D:
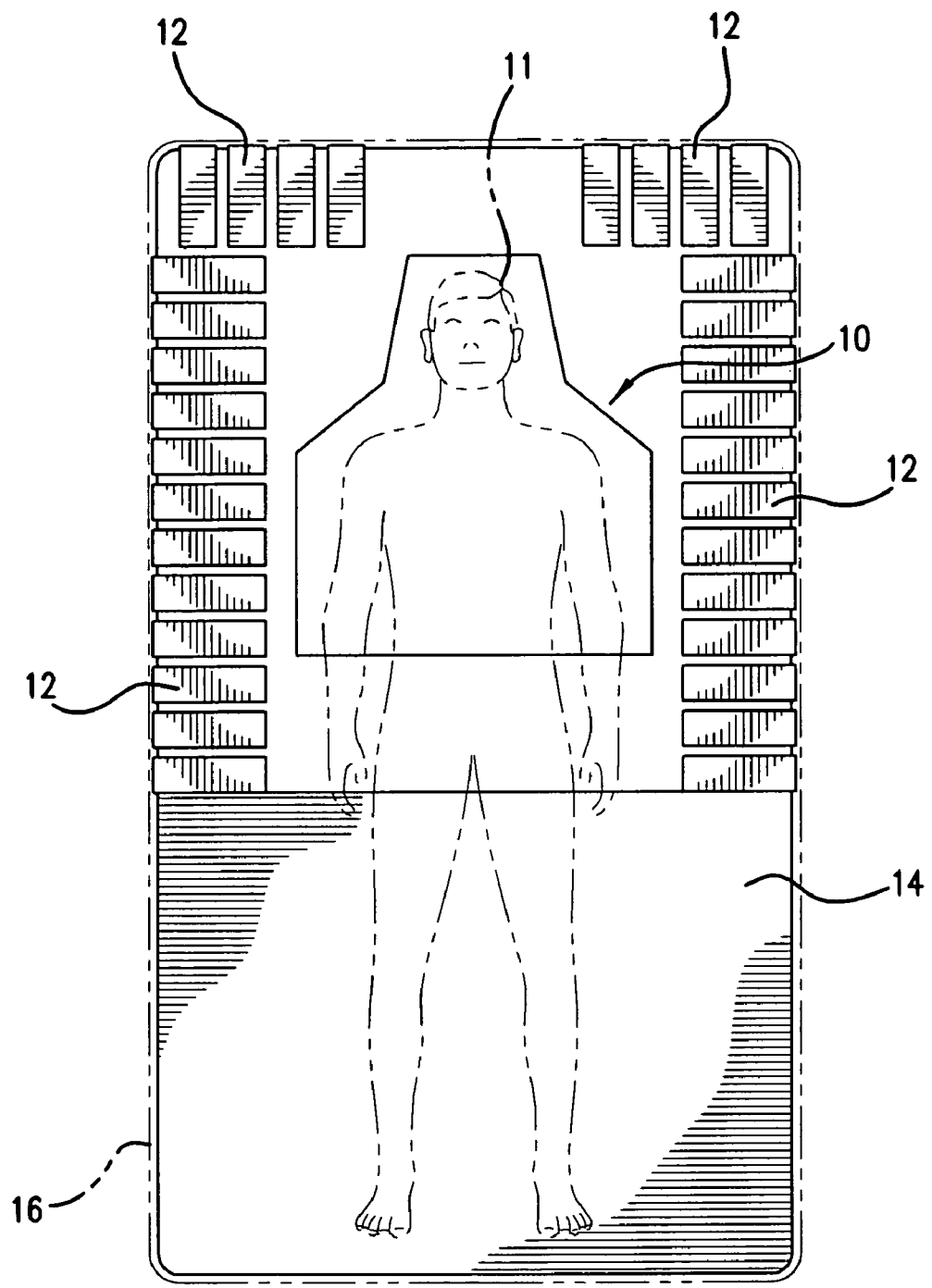
FIG. 1D shows a top view of a fourth embodiment of a therapeutic support surface in use. The bladder is shown as a "witch's hat" shaped void in the center to lessen bladder contact with parts of the body that may not be in need of cooling such as the head and shoulders. The generally rectangular bladder includes a void in the center to lessen bladder contact with parts of the body that may not be in need of cooling such as the head and shoulders.

A number of bladder shapes are possible and those depicted in FIG. 1A, FIG. 1D are not intended to be limiting. Also note that the conduction strips are much wider than seen in previous drawings. These broad conductive strips, or conductive plates, are compatible with any bladder configuration.

Figure 2A:
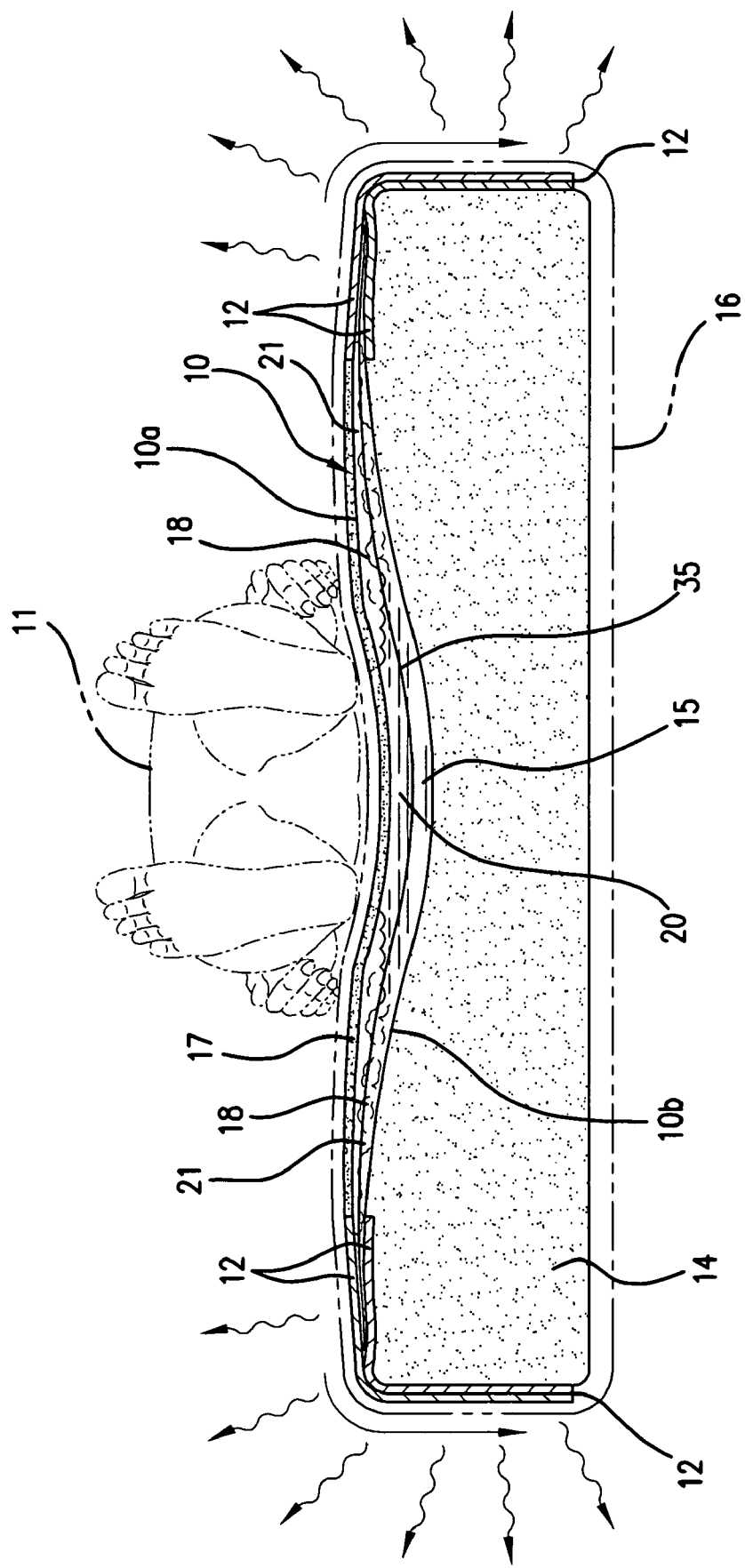

FIG. 2A is a cross-sectional view of one embodiment of the support surface pad, taken essentially along line 2-2 of FIG. 1A. In this embodiment, the cooling bladder is covered by a thin layer of foam, or an envelope containing gel or viscous fluid such as liquid silicone. This cushioning layer may also include particulate solid-to-liquid phase change materials (PCMs) with melting points between 80° F. and 94° F. This cushioning layer can cover the bladder and or conduction pathways completely or incompletely.

Figure 2B:
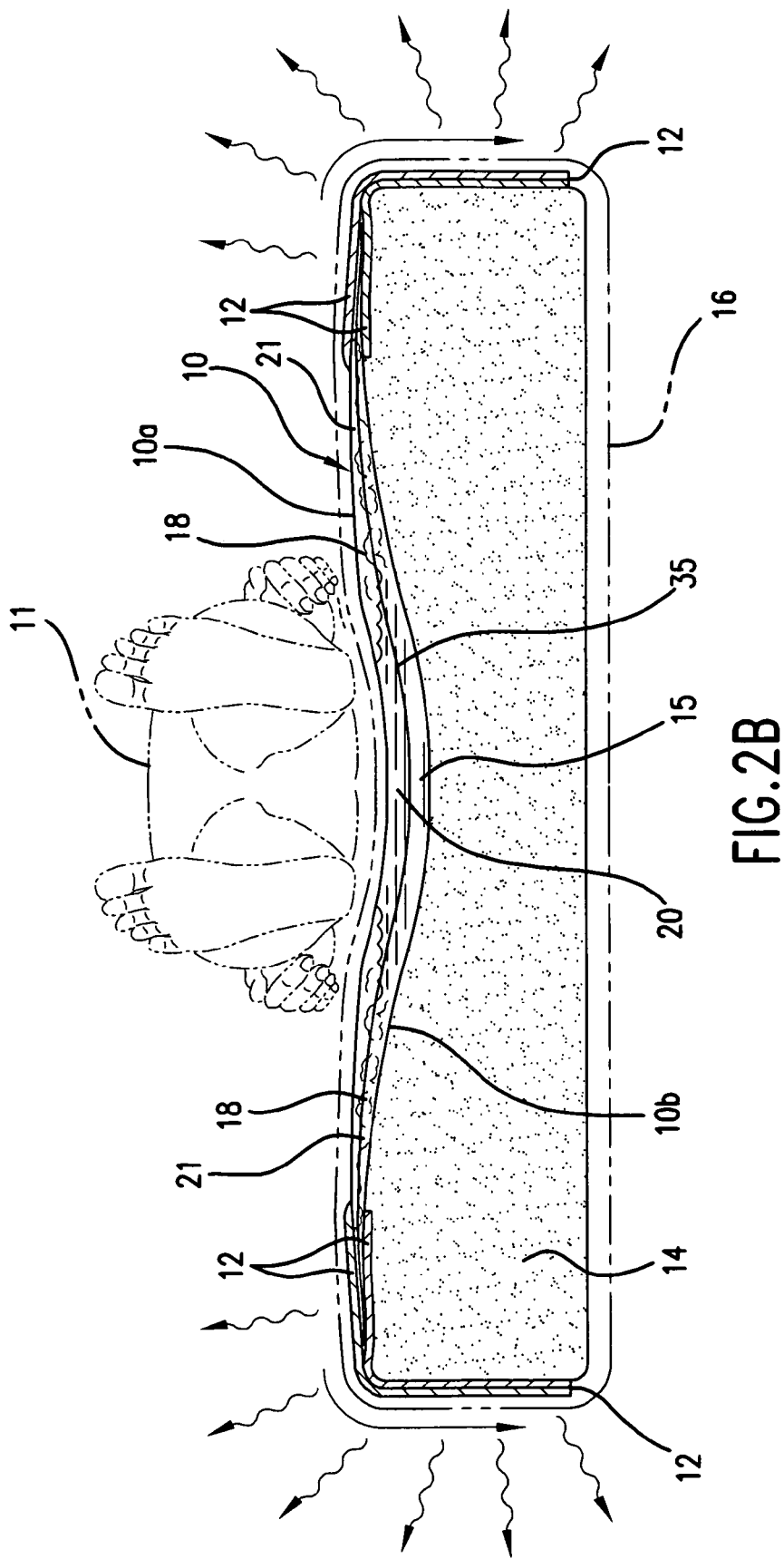

FIG. 2B is a cross-sectional view of a second embodiment of the support surface pad, taken essentially along line 2-2 of FIG. 1A. In this case, there is no foam, gel, or fluid cushioning between the bladder and the ticking of the mattress.

Figure 3:
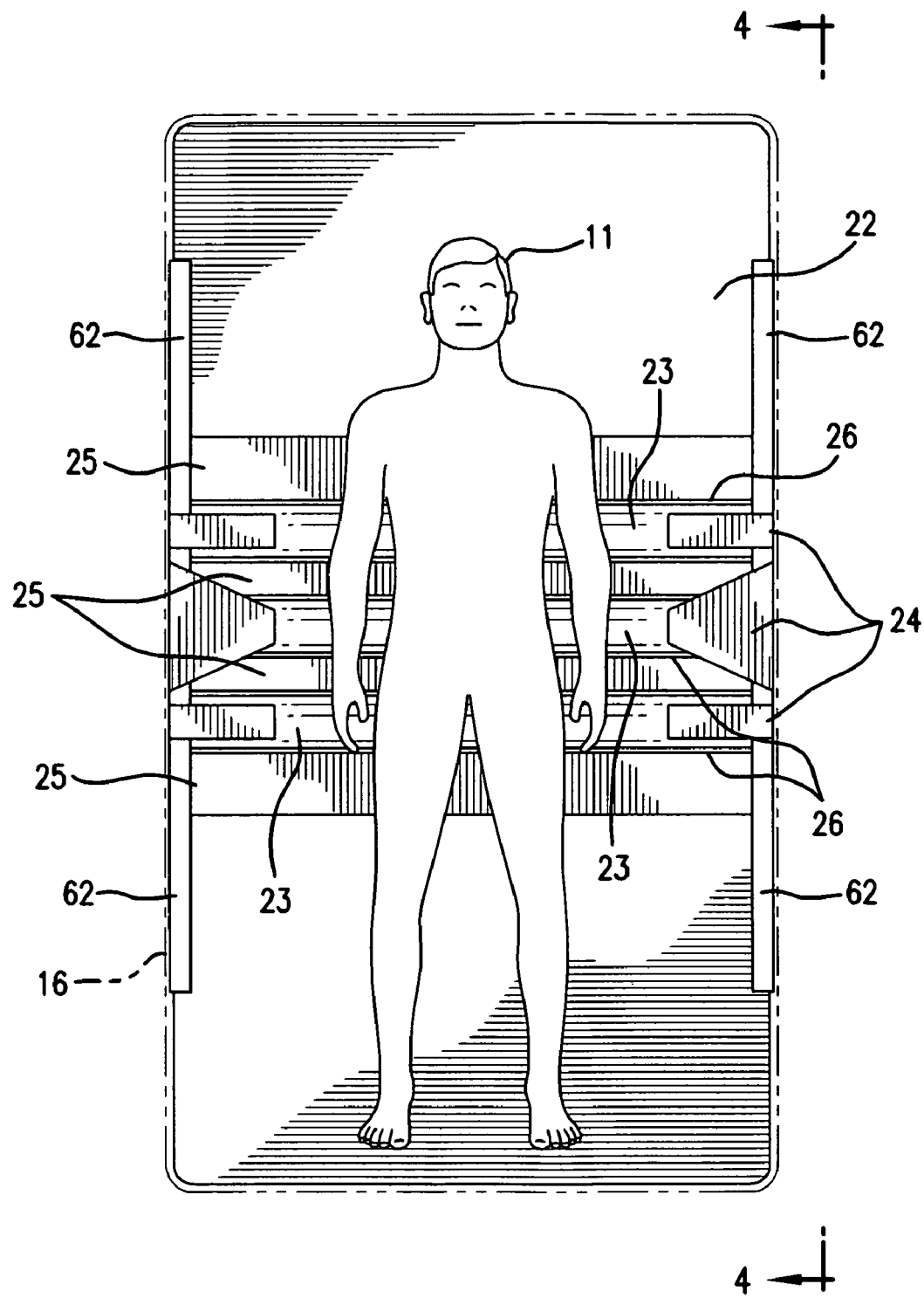

FIG. 3 is a top view of another embodiment of the support surface pad in use with or integrated into a foam or gel surface. In this embodiment, there are multiple independent bladders that run essentially parallel to one another across the support surface in the region of the skin to be cooled.

Figure 4:
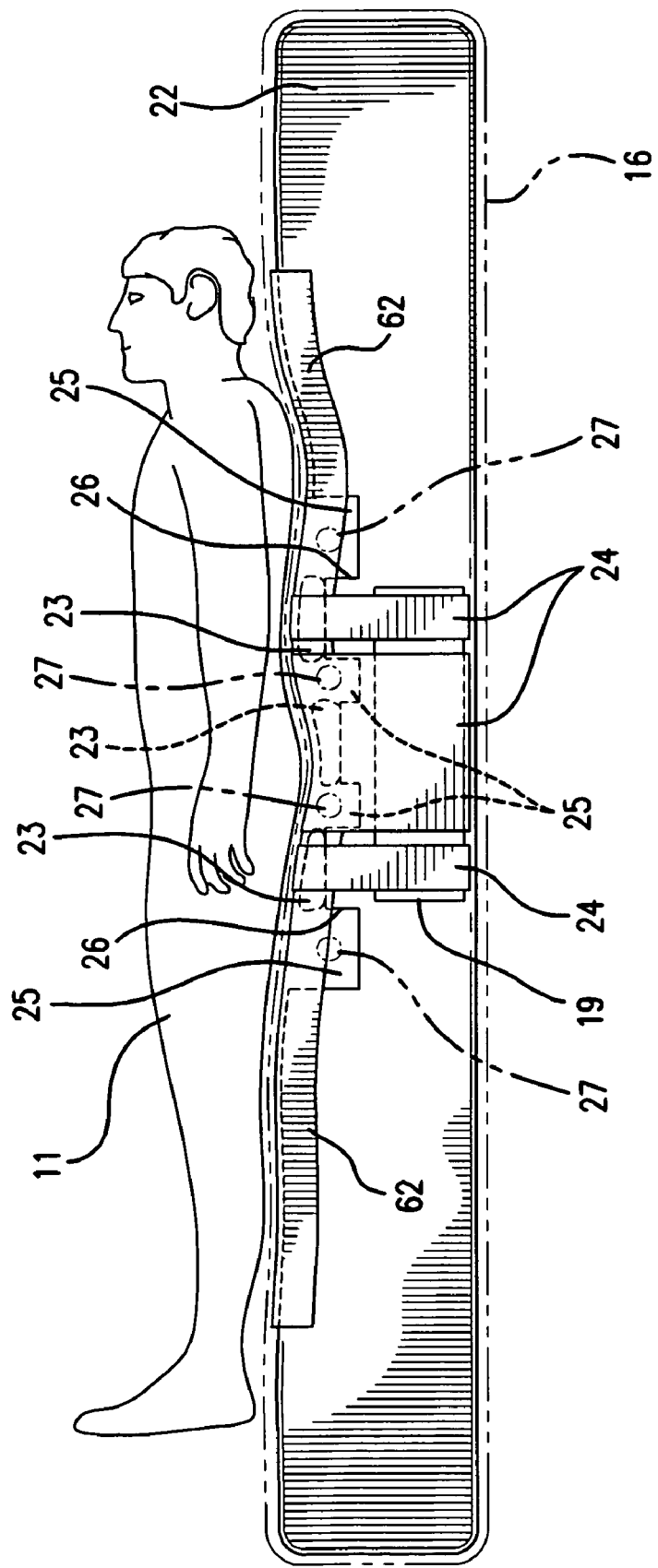

FIG. 4 is a side view of the embodiment shown in FIG. 3. The bladders rest on small pedestals and are separated by grooves in the surface of the mattress that allow limited airflow during use. Conduction strips extend from the edge of the bladder down the edge of the mattress and may extend to the bottom.

Figure 5:
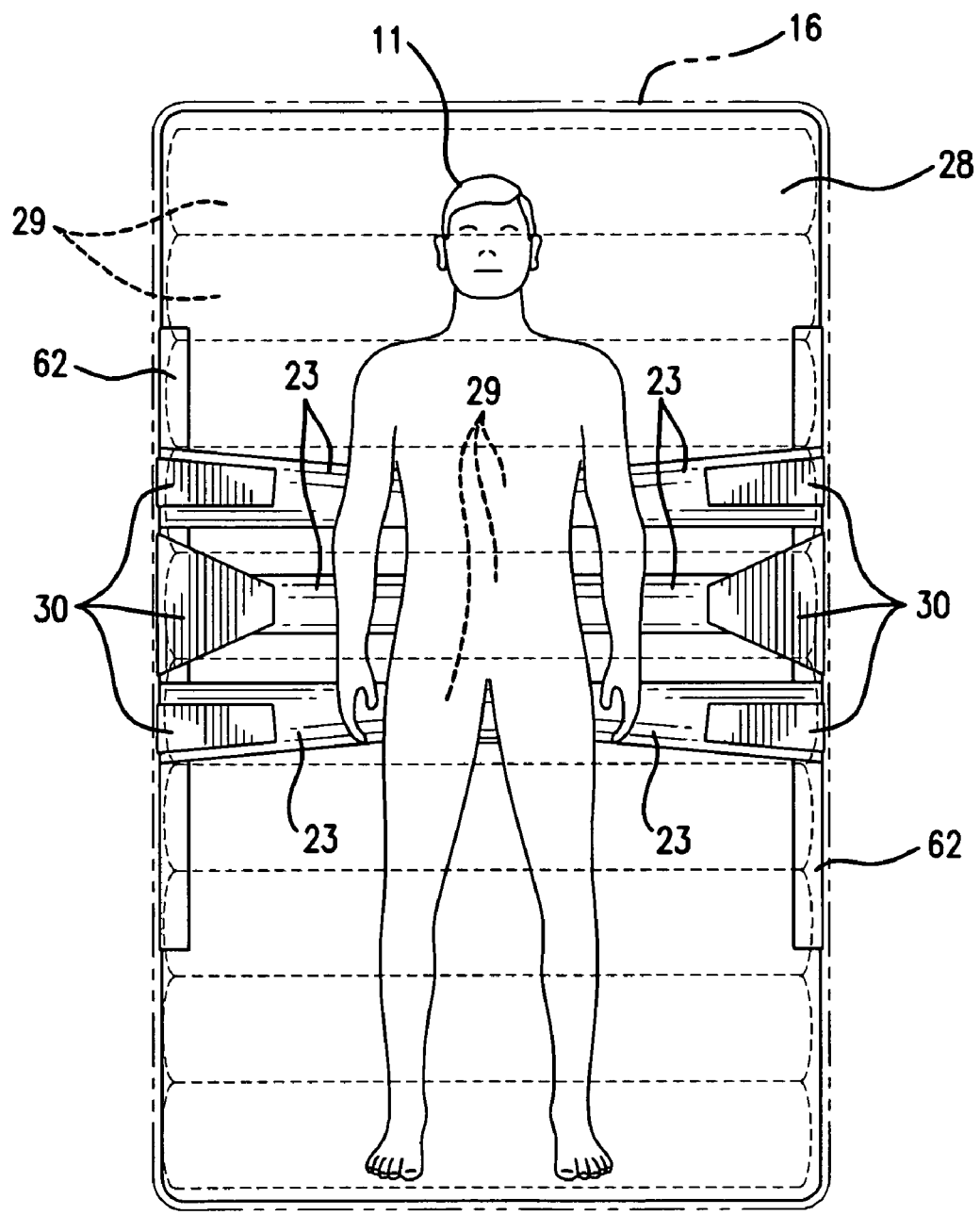

FIG. 5 is a top view of an embodiment of the device in use on an air mattress. In this embodiment, the bladders run side to side and rest on the air cells of the existing mattress. The bladders and conduction strips may flare or widen at the edges to aid with heat dissipation.

Figure 5A:
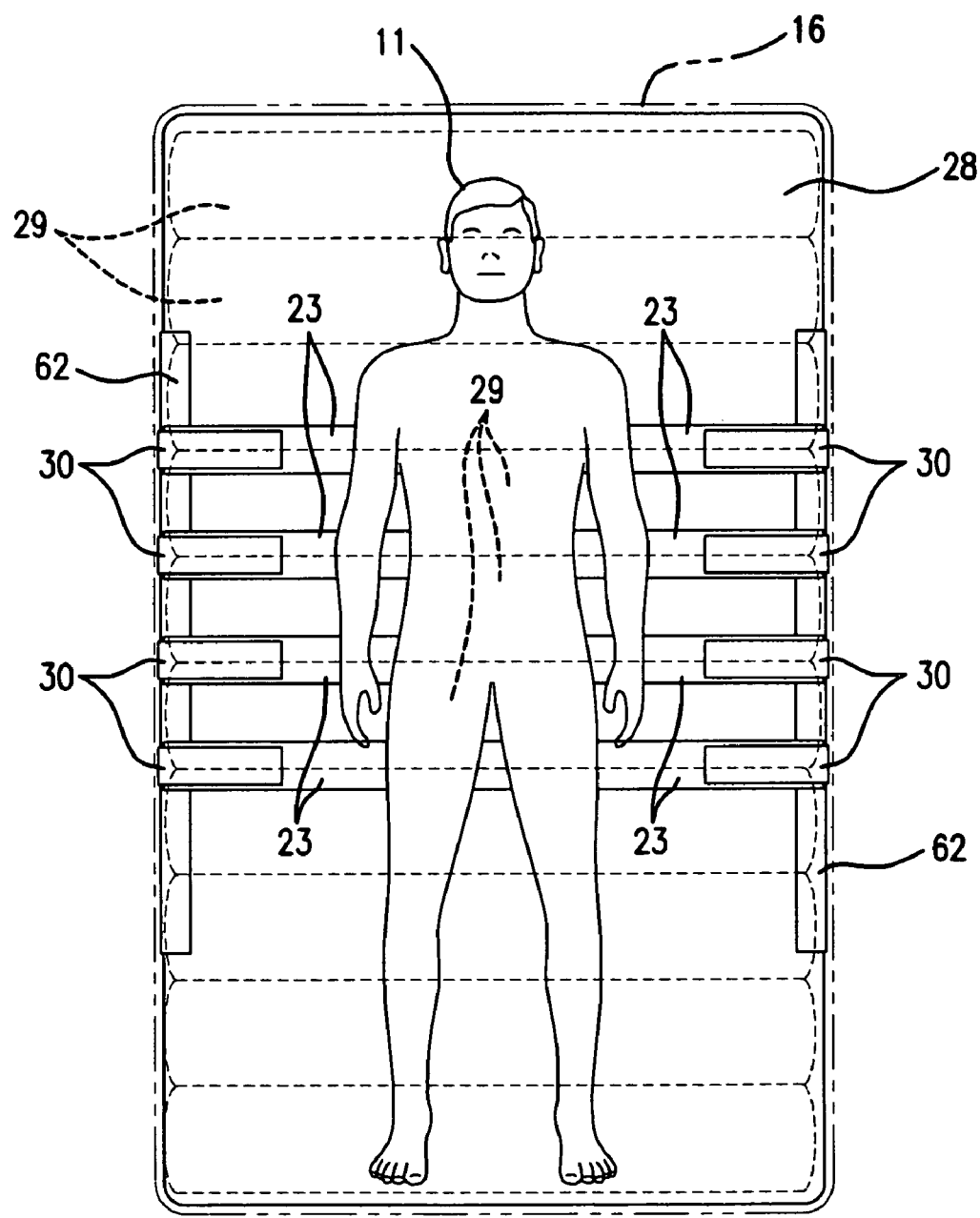

FIG. 5A shows gas bladders located between the air cells. Instead of resting on the top crest of the air cells, the bladders are nestled into troughs between these cells. The conduction strips are also shown connecting to an edge thermal diffuser strip. The conduction strips may extend around the edge of the mattress and across the bottom of the mattress.

FIG. 6 is a side view of the embodiment shown in FIG. 5. The cooling bladders rest atop the air cells of the air mattress with the conduction strips extending down the side of the mattress. The conduction strips may extend around to the bottom of the mattress and may flare prominently to enhance diffusion of body heat.

Figure 6A:
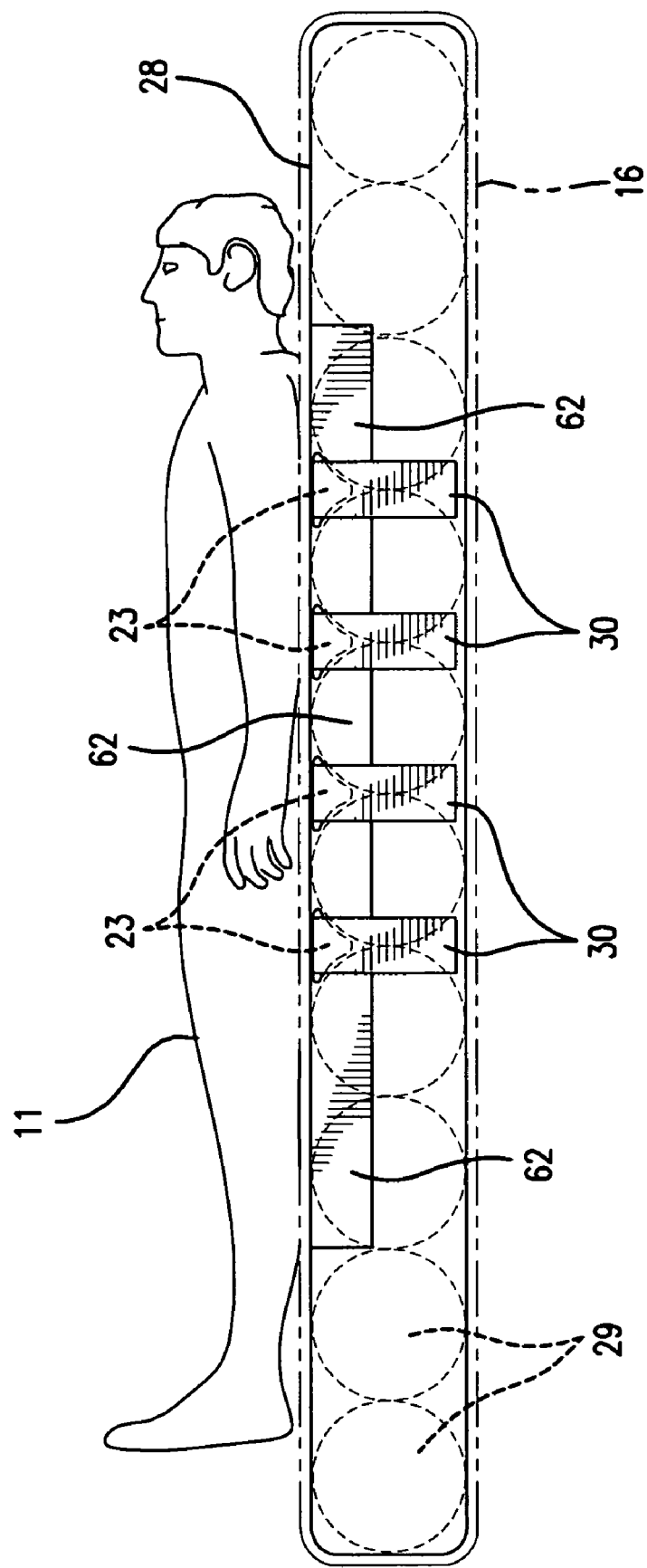

FIG. 6A is a side view of the embodiment shown in FIG. 5A in which the bladders are configured between the air cells, and the conduction strips enjoin an edge thermal diffuser. Either bladder configuration is compatible with either edge configuration.

Figure 7:
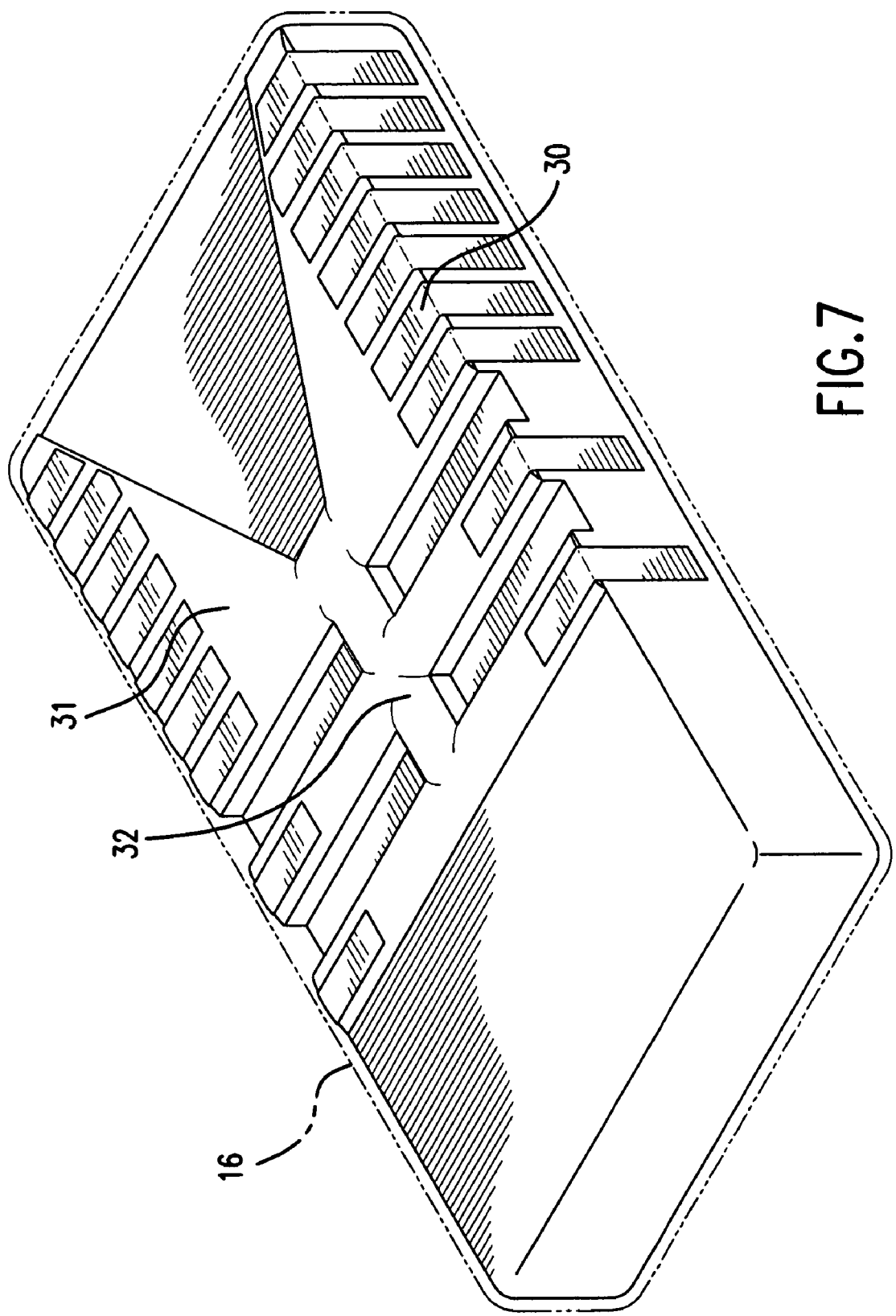

FIG. 7 shows a perspective view of an alternate embodiment of a therapeutic support surface and a cooling system according to the present invention. A small number of bladders are connected by a central channel that allows for gas or liquid transfer between chambers. There may be more than one communication channel.

Figure 8:
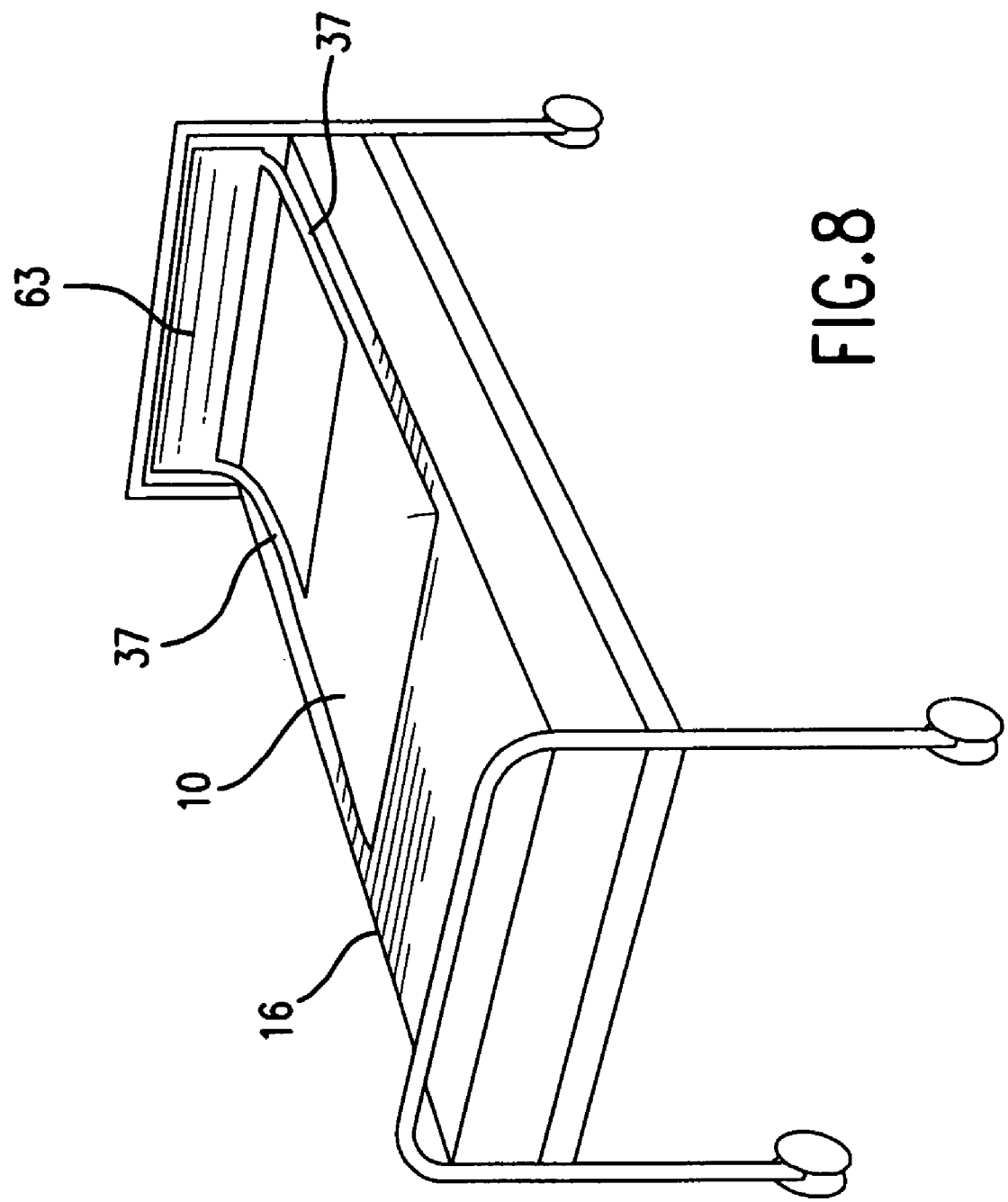

FIG. 8 is a perspective view of an embodiment in which the primary heat exchange surface is outside the ticking and positioned vertically or inclined at an angle above the occupant surface. The heat expansion surface is positioned on the headboard of the bed. The heat expansion surface may be otherwise suspended, for example, by suspending the heat expansion surface from a pole or rack associated with the bed frame, or from a frame that is independent of the bed. Conduits connect the bladder to the external heat exchange surface and allow for two-way communication of refrigerant vapor and condensed liquid.

Figure 9:
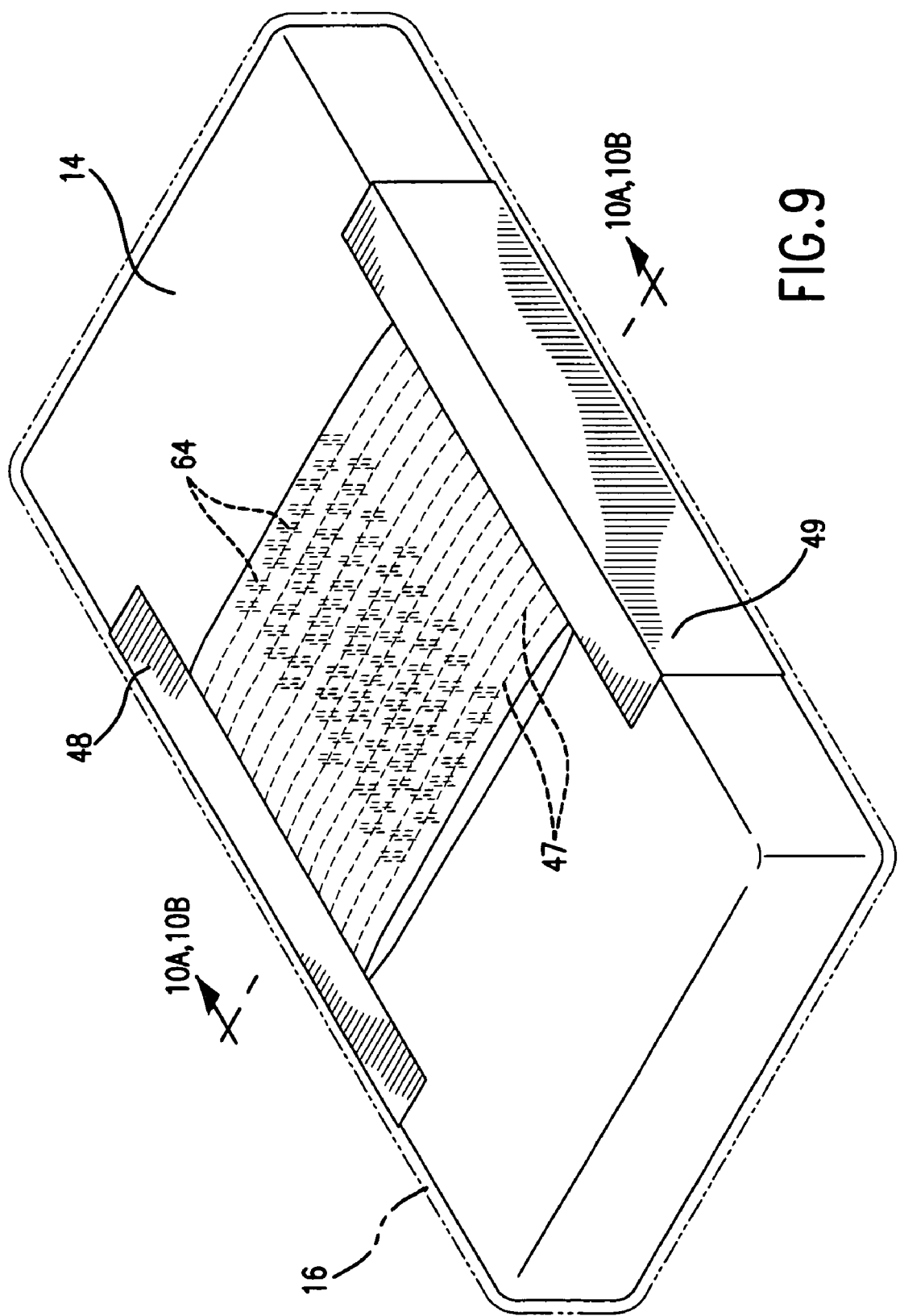

FIG. 9 is a perspective view of an embodiment of the conductive cooling device, wherein the device is positioned as an insert into a standard mattress and under the ticking. It can also be used as a seat cushion or seat back for wheel chair, home, office, or vehicle use. The device may be positioned outside the ticking or positioned as a mattress overlay, or positioned outside the seat cover as a seat overlay.

FIG. 9A is a perspective view of an embodiment of the conductive cooling device, wherein the device is positioned as an insert into a standard mattress and under the ticking as in FIG. 9. The conduction device may not have vertical conduction bundles as shown in FIG. 9. These vertical conduction bundles may or may not be present in all of the Conductive Devices depicted in FIGS. 9 through 16.

FIG. 10A is a cross-sectional view of an embodiment of FIG. 9 of the conductive device cut along the section line shown in FIG. 9.

FIG. 10B is a cross-sectional view of a very similar embodiment to that shown in FIG. 10A, also cut along the section line shown in FIG. 9. The only difference between these two is multiple layering of the conductive material in FIG. 10B, as opposed to the single, thicker layer shown in FIG. 10A.

Figure 10C:
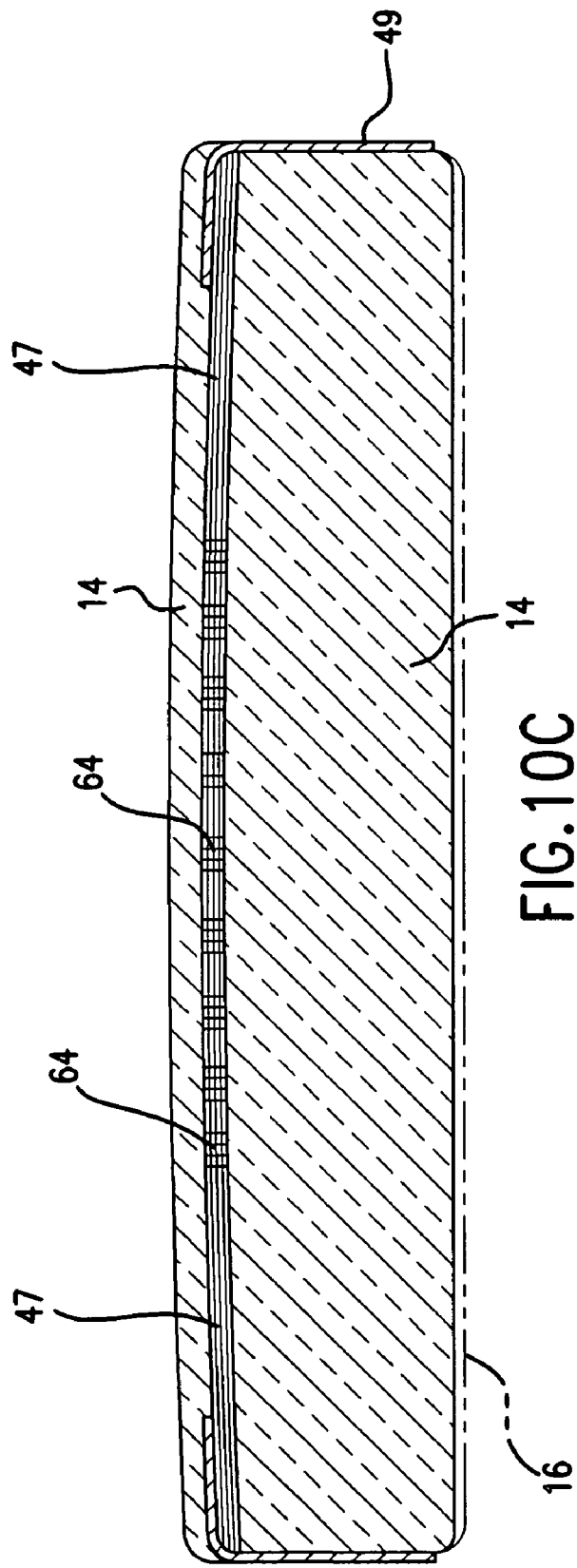

FIG. 10C is a cross-sectional view of an embodiment in which the conductive layer is located under a thin cushioning pad. Note that these vertical conduction bundles (64) may or may not extend through this pad. The cross-section is again cut along the line shown in FIG. 9.

FIG. 11 is a perspective view of an embodiment of the conductive cooling device, wherein the device is positioned as an insert into a standard mattress, and under the ticking. The device may be used as a seat cushion or seat back for wheel chair, home, office, or vehicle use. This embodiment is distinct from that of FIGS. 9 and 10 in that the conductive material in FIG. 11 is embedded in a cushion of foam, elastomer or gel material, whereas in the previously-shown embodiment, the conductive material was essentially bare, and bound into a fiber bundle or in sheeting layer(s), without surrounding material for cushioning and added strength.

FIGS. 12A and 12B are cross-sections of the embodiment shown in FIG. 11. The distinction between FIGS. 12A and 12B is that in FIG. 12B, the conductive fibers are separated into multiple layers, whereas they form a single conductive layer in FIG. 12A. Also note that FIG. 12A is configured for use inside the mattress ticking while FIG. 12B is configured outside the ticking. All devices presented may be positioned inside or outside the mattress ticking or seat cover.

Figure 13A:
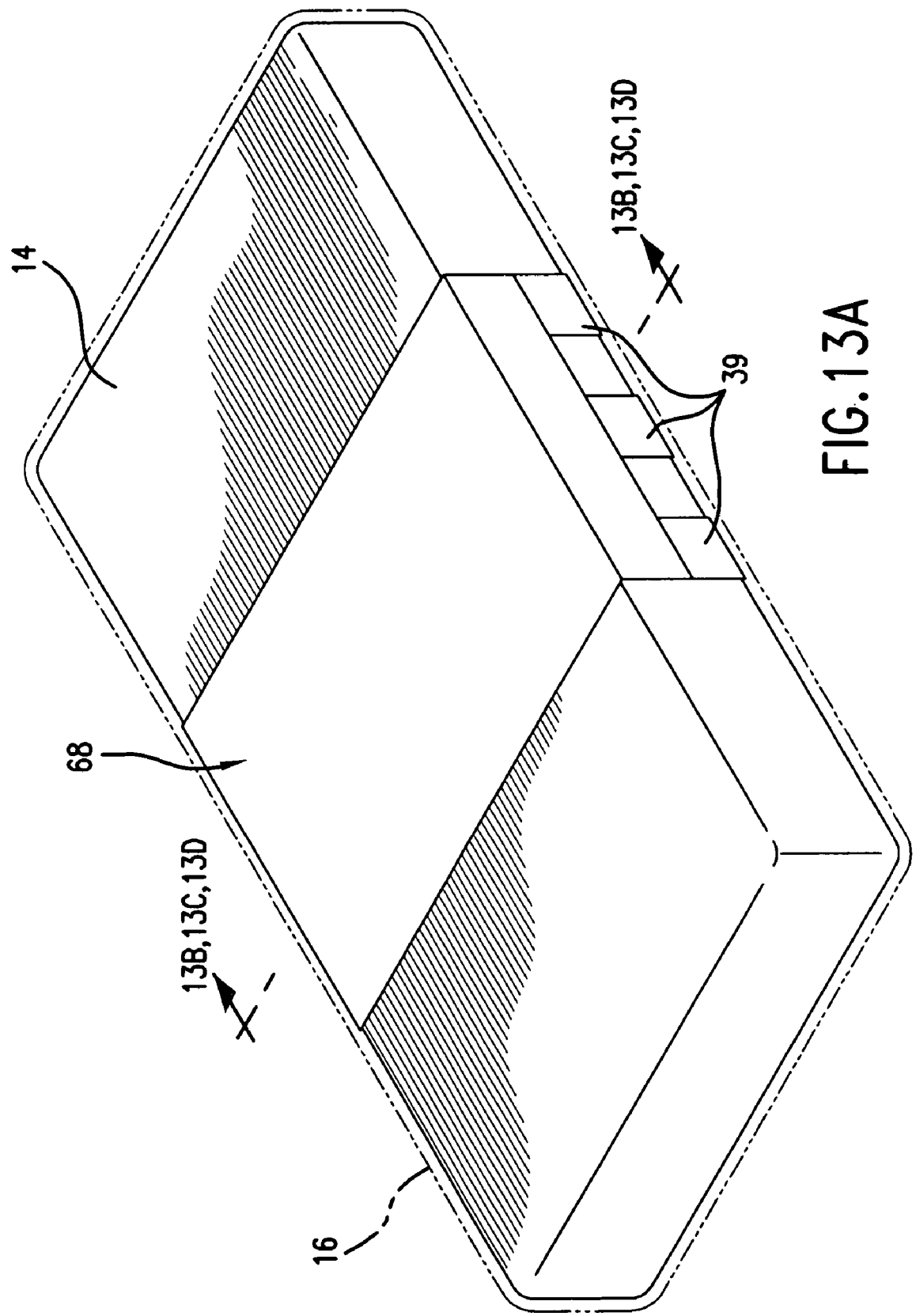

FIG. 13A is a perspective view of a conductive device positioned in the lower torso region within a mattress.

Figure 13D:
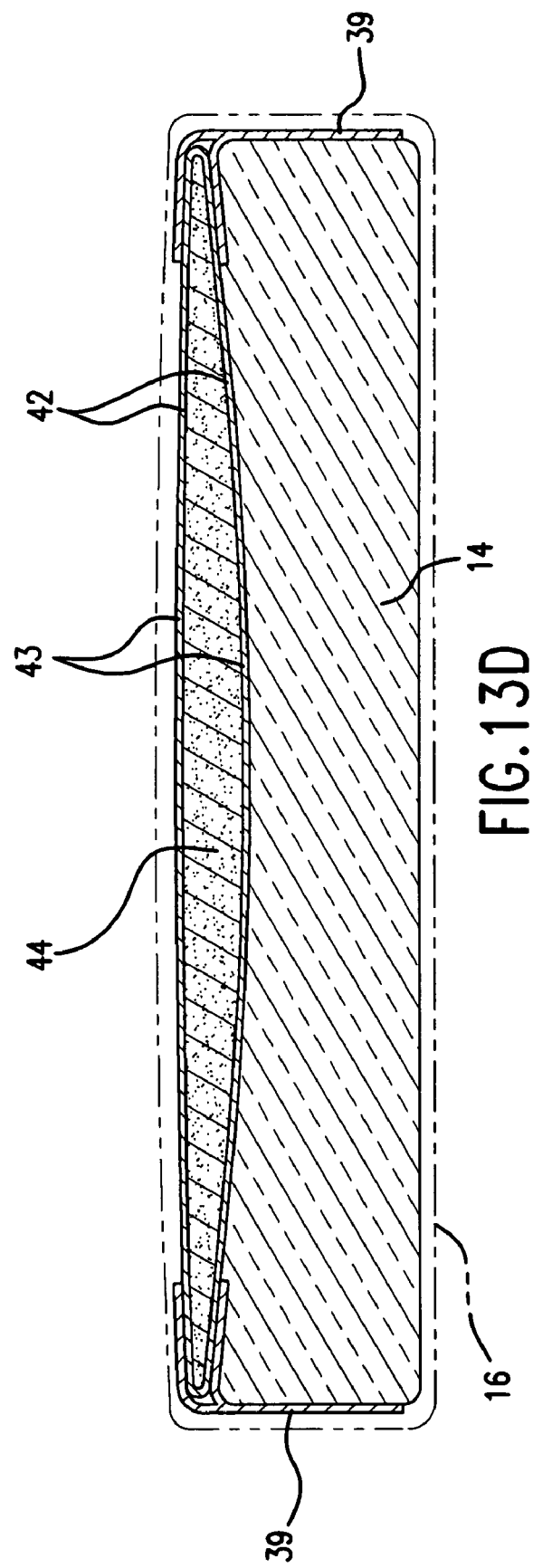

FIGS. 13B, 13C, and 13D are additional embodiments of the conductive device cut along the line shown in FIG. 13A. The essential distinction between this group and the embodiments shown in FIGS. 9-12 is that the conductive material may be embedded in a cushion or gel, elastomer, foam, or viscous fluid, and is also surrounded by a compliant envelope. That is, in the embodiments depicted in FIGS. 13 A, B, C, and D, the conductive layer itself is surrounded a compliant envelope. The conductive fibers within this layer may or may not be embedded in a gel, elastomer, foam, or viscous fluid.

Figure 14B:
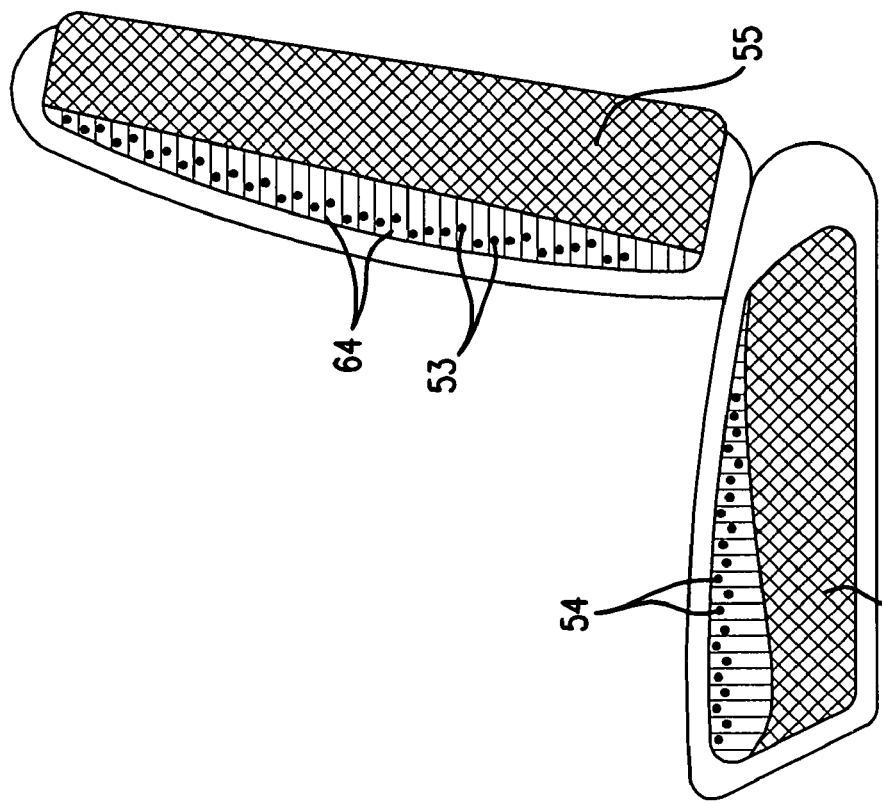
Figure 14A:
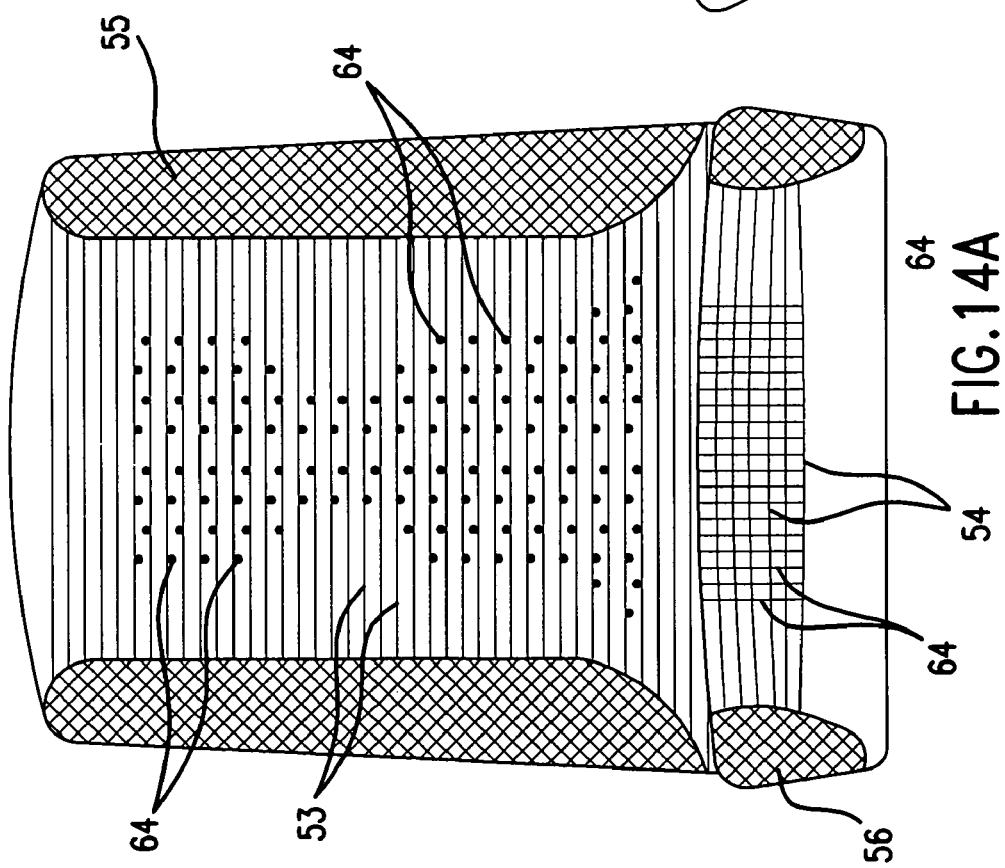

FIG. 14A is a front view of a seat and seat back outfitted with the conductive cooling device. This could be for medical, vehicle, office, or home use.

FIG. 14B is a side view of the seat depicted in FIG. 14A.

FIGS. 15A and 15B are side views of a conductive devices in use on an air mattress. In FIG. 15A, the conductive layer is shown on top of the transverse air tubes. In FIG. 15B, these conductive fibers are nestled into the troughs between air cells. Alternatively, the conductive fibers maybe between air cells or spread in a continuous sheet. They may be built into the ticking as shown below.

Figure 16A:
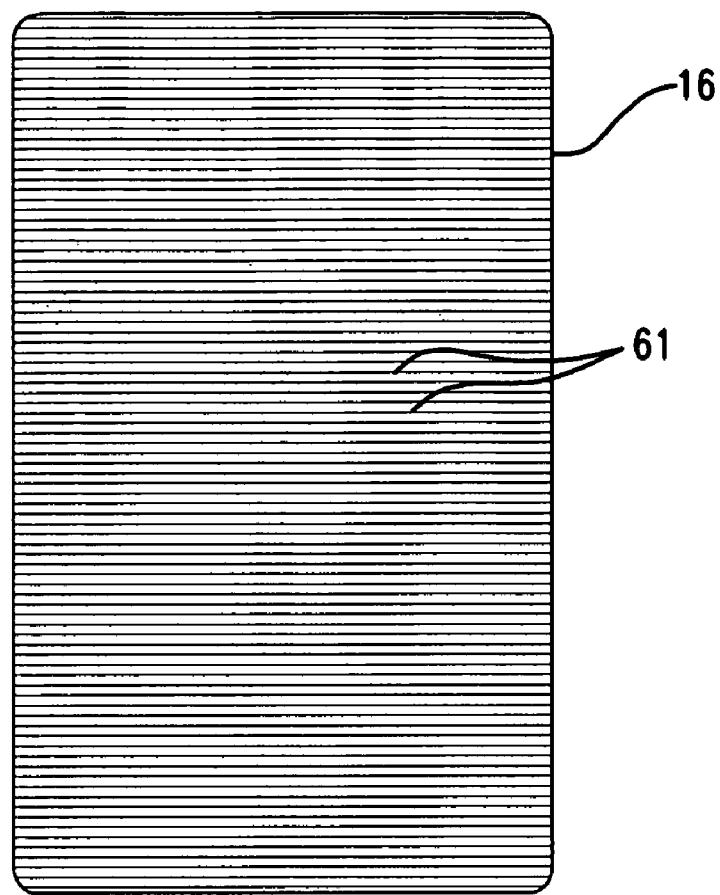

FIG. 16A shows a top view of an additional embodiment is which the highly conductive fibers are actually attached to the underside of, or incorporated into (between layers of), the ticking.

Figure 16B:
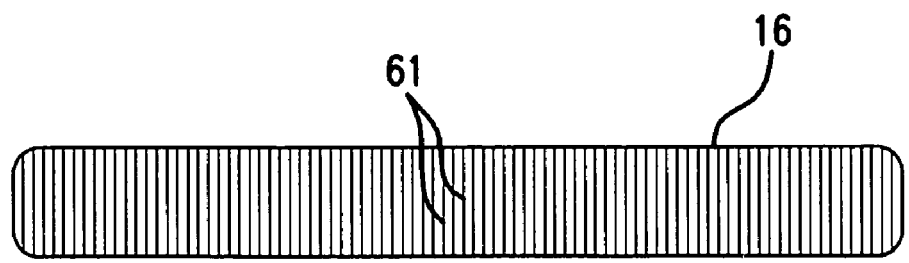

FIG. 16B is a side view of the highly conductive fiber built into or attached to the ticking. Note that the fibers extend down around the edge of the mattress (or seat surface or seat back) and may extend to the reverse side.

DESCRIPTION OF THE PREFERRED EMBODIMENTS

Summaries of Preferred Embodiments. The prototype devices described have been designed to moderately reduce skin temperature as an aid to pressure ulcer treatment and prevention. More accurately, the devices described limit significantly the warming of the skin that occurs when uncovered skin is insulated by contact with a mattress, seat, or seat back. (This is often referred to as "relative cooling", because the skin is cooled relative to its temperature under standard insulated conditions of support but may still be somewhat warmer than uncovered skin.) The devices also have a number of comfort-related applications in non-medical situations such as automobile or truck seats, office furniture, or mattresses for the home.

In contrast with a conventional mattress or other resting surface, such as a wheelchair seat cushion or general seating, the support surfaces of the present invention distributes heat away from the user's body during the support period. This keeps the user more comfortable while sleeping or sitting, particularly under the user's bony prominences, i.e., regions of high interface pressure such as the sacrum, where bedsores are more likely to form. Relative cooling is accomplished in one class of embodiments, referred to collectively as the "Gas Expansion Devices", by a central, refrigerant-containing bladder (or series of smaller bladders) connected to thermally conductive pathways that distribute heat from this central region(s) to the cooler periphery of the support surface. A second class of embodiments (referred to here as "Conduction Devices") makes use of highly conductive material that may be embedded in a gel, elastomer, foam, or fluid to create a layer that is capable of rapidly transporting heat from the warmer portions under the occupant to the cooler regions at the periphery of support via conduction, where thermal diffuser(s) release this heat to the surroundings. This conductive layer can also be incorporated into the ticking or seat cover by adhesion, or woven directly into it. Both classes of inventions may employ microencapsulated solid-to-liquid phase change materials dispersed in a gel, elastomer, or fluid, and contained in a pliable envelope to enhance thermal stability at the selected temperature of phase change. Cooling is ideally held to a narrow temperature range just below normal insulated skin temperature, since cold temperatures are uncomfortable and undesirable, particularly where the occupant is emaciated or otherwise infirm. The desired skin temperature range is 30° C. to 34° C., although conventional support surfaces typically trap the body's heat and warm the skin rapidly to approximately 35° C. to 37° C. In fact, the degree of cooling achieved by the inventions brings the skin approximately to its natural temperature under non-insulated, thermo-neutral environmental conditions. Thus, in addition to making the user more comfortable, the present invention reduces the likelihood of bedsore formation, and aids in the healing of early stage bedsores or other skin ulcers that the user may already have. Since the user's skin is held to a temperature below perspiration threshold (approximately 32-34° C. or 91-93° F.), the user is relatively free of perspiration. This also contributes to skin health, since moisture build-up weakens the skin and makes it more susceptible to tearing and consequent infection. Most significantly, the tissue is less susceptible to injury caused by reduced blood flow caused by pressure at the skin/support surface interface, because reduced skin temperature has been shown to markedly reduce the demand of the skin tissue for oxygen and nutrients.

Embodiments of the Gas Expansion Device, depicted in FIGS. 1 through 8, are described below.

A preferred heat exchange support surface for added comfort, maintaining a cool skin temperature, or reducing the incidence and promoting the healing of bedsores, includes:

(a) a central portion comprising a hollow, enclosed bladder containing a pre-determined amount of liquid refrigerant, the refrigerant having a boiling point between about 23° C. and about 35° C.

(b) a thin, flexible spacer mechanism contained in the bladder, the spacer mechanism separating an upper bladder wall from a lower bladder wall. This spacer mechanism may have the surface converted with a radicalized halogen or other species to optimize surface interaction with the refrigerant and enhance condensation and the efficiency of heat exchange.

(c) thermally conductive end portions attached to opposite ends of the bladder, the conductive end portions comprising a heat conductive material layer. These may extend: (1) from the outer border of the bladder (with substantial overlap onto the bladder) and radiate outward from all borders; (2) around the edge of the mattress, seat, or setback, to the underside of the mattress or seat or backside seat back. The strips that extend beneath the mattress may transfer heat directly to the bed frame, further increasing the area for heat diffusion to the environment. Depending upon heat transfer conditions, these conductive strips or plates may be much shorter, extending only one to two inches from the edge of the bladder. These thermally conductive end portions may or may not be attached to the outer wall of the bladder using thermally conductive greases, epoxies, and the like to enhance heat transfer (d) this cooling device can be incorporated into a conventional mattress, or it can be used as a separate device that can be used with an existing mattress to enhance skin cooling. It can also be incorporated into or used as an overlay on a seat cushion or seat back for wheel chair, office, or vehicle applications.

(e) the central bladder can be rectangular in shape but may take a range of configurations as shown in FIGS. 1A, B, C, and D to minimize the heat load from portions of the device that do not require cooling, and to maximize bladder exposure to cooler, ambient air. It may also flare to a wider dimension with distance from the region of the body to be cooled. This flaring can take a symmetric shape (such as a bow-tie when viewed from above), or it can take an asymmetric form to increase bladder cooling and conduction path area in cooler regions of the surface. For example, a preferred embodiment involves flaring of the side regions of the bladder and conduction area upward so that they extend up from the waist and to either side of the head. The bladder may also be formed by joining two separate bladders along the center line to aid the manufacturing process.

An alternate embodiment involves the following: heat exchange support surface for added comfort, maintaining a cool skin temperature, or reducing the incidence and promoting the healing of bedsores, includes:

(a) a series of independent hollow bladders containing a pre-determined amount of liquid refrigerant, the refrigerant having a boiling point between about 23° C. and about 35° C., which may be adjusted to meet specific thermal requirements;

(b) thin, flexible spacer mechanisms contained in some or all of the bladders, the spacer mechanism separating an upper bladder wall from a lower bladder wall. This spacer mechanism may have the surface converted with a radicalized halogen or other species to optimize surface interaction with the refrigerant and enhance condensation and heat exchange efficiency.

(c) thermally conductive end portions attached to opposite ends of each bladder, the conductive end portions comprising a flexible heat conductive material layer to transfer heat from the edge of the bladder to the environment, perhaps via the bed or seat frame.

(d) this device can be incorporated into a conventional mattress (such as a foam, gel, or air mattress), or it can be used as a separate device that can be used with an existing mattress to enhance skin cooling. It can be positioned either inside the ticking or seat covering or outside the ticking or seat covering as an overlay.

(e) these bladders may or may not be connected mechanically, but there will be no communication between bladder chambers for liquid or gas flow.

In an alternate embodiment, the device is configured as described above with the following exception: the multiple bladder configuration does allow for liquid or gas flow between these otherwise isolated bladders. A central tube or a small number of tubes communicates between these bladders that are otherwise relatively independent from a mechanical standpoint.

In an alternate embodiment, the device comprises two large bladders joined at the center-line. Liquid and gas may or may not communicate between bladders. As above, the bladders are constructed of gas-impermeable material, including the spacer material, and are rimmed with thermal conduction material such as copper to draw heat away from the bladder.

In an alternate embodiment, any of the above bladder configurations may or may not include internal conductive metal strips, wires, or metal "wool" to aid heat exchange.

In an alternate embodiment shown in FIG. 8, essentially the same principles are used, but the heat exchange diffusion surface is positioned outside the ticking, and suspended in the vertical plane or inclined at an angle at a level slightly above the support surface. Small ducts connect the cooling bladder to the external heat exchange diffusion surface, allowing for two-way communication of both vapor and condensed liquid refrigerant.

The proximal region of the heat exchange support surface is the region that supports the parts of the occupant's body that are the "target areas" of the occupant's body to be cooled by means of the heat exchange support surface. In a preferred embodiment, the proximal region is the part of the heat exchange support surface that is immediately under or adjacent to the hips and torso, and will be a central region of the support surface. The distal region of the heat exchange support surface refers to the areas of the surface that are not usually covered by, and, in most circumstances, do not materially contact, the occupant, such as the sides and edges of a mattress, seat, or seat back. In a preferred embodiment, the distal region will be the peripheral area of the support surface that is remote from the central region. Heat that has been withdrawn from the occupant's skin in the proximal region of the support surface is exhausted to the environment in the distal regions of the support surface.

The term "non-powered" as used herein means that, if we consider the system as consisting of the surface and the occupant, there is no input of external power to the system, other than perhaps some relatively inconsequential ambient heat. Because the only flow of power into the surface is the input of body heat from the user, the system may also be referred to as comprising a "self-powered" cooling surface. While most of the embodiments discussed herein are non-powered, some embodiments also include provision for external power input.

The region of the bladder where refrigerant collects in the proximal part of the bladder (i.e., immediately under or adjacent to the occupant) may be referred to as a "pocket". The deformable nature of the bladder means that the precise location and shape of the pocket may change somewhat in response to movements of the occupant as he or she shifts their body and the weight thereof. The pocket does not have a specific location or feature in the bladder, but it is located in the region of the bladder that is covered by, and is pushed downward by, the weight of the occupant, and is therefore in a lower portion of the bladder. Since the pocket is in a lower portion of the bladder, it naturally receives the return flow of condensed refrigerant, due to gravity.

The cushion is a deformable substrate that comfortably supports the occupant. In this context, the cushion:

has a degree of mechanical compliance. In this context, if the cushion or the compliant material is placed in the center of a standard hospital mattress, a standard 1.0 kg steel ball, when placed in the center of the support region will cause the surface of the cushion or deformable material to compress by greater than or equal to 0.25 mm.

will be located in the region of the support surface such that the cushion will directly or indirectly support the occupant at some time during use.

A second class of embodiments relies primarily on rapid conduction of heat, rather than the fluid expansion that accompanies liquid to gas phase change, to transport heat from the region to be cooled. The Conductive Devices FIGS. 9 through 16 have a layer or layers of highly thermally conductive material, typically highly conductive fibers such as pitch-based carbon fibers, configured in the specific manner described in Tables 1 and 2. This conductive layer or layers may comprise essentially bare conductive fibers, or these fibers can be embedded in an elastomer, gel, or foam cushion to provide protection to the fibers and enhance comfort. Alternatively, the layer(s) may be enclosed in a soft pliable envelope that may also include elastomer, gel, or viscous fluid such as liquid silicone or urethane with dispersed particles or fibers of highly conductive material such as chopped carbon fiber, copper or aluminum. This conductive layer will be somewhat compliant, as it extends across the central portion beneath the occupant in a mattress, seat, or mattress overlay, or against the occupant in a seat back application. A preferred embodiment includes continuous carbon fiber filaments that are oriented primarily perpendicular to the periphery of the body to enhance heat transport away from the body. That is, the filaments will generally be oriented transversely to the mattress, seat, or seat back, such that heat flow along the length of these fibers is directed away from the body. Shorter conductive fiber bundles may be used in the central section, most directly supporting the warmer region of the body, that are oriented perpendicularly to the surface to aid in heat transport to the deeper conductive layers. Many high-conductivity, compliant materials, such as carbon fibers, exhibit non-uniform conduction properties. Although these fibers conduct heat extremely well along their length, there is little transfer of heat perpendicular to this direction and into the adjacent parallel fibers. The deeper layers may provide little benefit with respect to heat transfer without these fibers oriented perpendicularly to the surface. This compliant conductive layer may lead to, with or without overlap, inwardly-projecting conductive strips or sheeting such as plates of copper (conductivity=400 W/m-K) or aluminum (conductivity=170 W/m-K), or similar thermally conductive material toward the edges of the support surface that serve to thermally bridge the conductive layer to the thermal diffuser with a less expensive, less compliant conductor. Typically, the compliant central conductive layer will make use of carbon fiber, and these inwardly-projecting strips, when present, will be composed of much less expensive copper or aluminum. Alternatively, the conductive material itself can extend fully across the occupant support region and into the exhaust zone so that it connects directly to, or functions as, the thermal diffuser to the environment. The enclosed inwardly-projecting cooling sheets or plates, when present, may be angled downwardly from the edges slightly to enhance comfort, if the occupant should happen to sit or lie directly above it. The enclosed cooling plates, sheets, or strips, when present, will be attached to side or edge plates (thermal diffuser) at the edge of the mattress or seat to diffuse heat directly to the environment. These diffuser plates can be limited to the top periphery and/or vertical edge of the support surface, or they can extend around to the bottom or back side, depending on variety of heat transfer parameters such as ambient temperature, occupant cooling required, material used for these plates, and thickness. These extended cooling plates that extend underneath the mattress may be particularly effective in that they can transfer heat to the bed frame itself (which is typically quite thermally conductive), increasing further the are for heat transfer to the environment. The above assembly could be used as a cooling seat cushion, seat, back, or a cooling insert to a mattress, or as an overlay to be used on top of the mattress ticking or seat.

There are four basic ways in which this highly conductive layer can be constructed, but each has in common a number of characteristics to accomplish the tasks of physiologic thermal management. The conductive layer may:

- comprise highly conductive materials embedded in a cushion or cushions of gel, foam, or elastomer; or
- comprise highly conductive materials embedded in a fluid, gel, foam or elastomer and surrounded by a fluid-impervious envelope; or
- comprise highly conductive materials not embedded in a fluid, gel, foam or elastomer but surrounded by a compliant envelope; or
- comprise a layer of highly conductive materials not embedded in a cushion or envelope but simply configured in a specific manner, described herein, to accomplish the thermal management task.

Another simple alternative embodiment makes use of chopped carbon fiber or other conductive material such as powdered aluminum, dispersed in a foam, gel, elastomer or fluid medium. In such cases, all other factors are as described above with the exception that the conductive cushion composed in this way has no oriented conductivity. The entire cushion will conduct heat toward cooler regions, again at the periphery where the thermal diffuser sheeting or strips will diffuse this heat to the environment.

All embodiments discussed above may or may not also make use of the solid-to-liquid phase change for the initial energy absorption to provide an additional measure of thermal stability at the selected temperature of phase change. Phase change materials (PCMs), if used, serve to delay skin warming. In these embodiments, PCMs do not materially contribute to steady state cooling. Also in these embodiments, a phase change material (encapsulated or non-encapsulated) is dispersed in a fluid or a gel that may be confined in a pliable envelope such as urethane film and positioned immediately under the ticking to form a temporarily cool, comfortable, compliant patient support surface.

Details of Preferred Embodiments

Turning to FIG. 1A, a skin cooling surface or device helps to maintain comfort, reduce the incidence of, and promote the healing of bedsores (decubitus ulcers) and the like in persons using the support surface. This cooling surface may be in the form of a pad 13 that is placed over a conventional mattress 14, as shown in FIG. 1A. Typically, the pad is inserted under the mattress ticking, but it may be placed directly on the outer surfaces of the mattress for enhanced cooling. Alternatively, the pad may be used in conjunction with other mattress overlays. For example, the pad may be placed directly on the surface of a mattress but underneath a second overlay that has additional properties of interest, such as superior comfort or cushioning characteristics. This support surface may also be a panel that is built directly into a conventional mattress. The support surface or pad 13 may be used in private homes, hospitals, clinics, long-term care facilities, hospices, etc. Support surfaces according to the invention are preferred to be relatively lightweight, easy to store, and may be easily cleaned between patients or other users.

Referring to FIGS. 1A, B, C, and D, preferred embodiments of a cooling pad 13 are comprised of a central bladder portion 10 that are connected to two opposite, matching, flared regions at the periphery of the mattress. In the preferred embodiment of FIG. 1A, the bladder edges project upwardly from the waist in an "angel wing" configuration that increases the surface area for cooling in the cooler regions of the bed (i.e., to the sides of the head where the bladder will not be covered by blankets to trap heat). Note that the radiating dashed lines in the top center of FIG. 1A indicate that a number of bladder shapes are possible, with the greatest ratio of peripheral "cooling bladder area" to central "cooled skin area" providing the greatest cooling power. Thermally conductive strips 12 are preferred to overlap at least 1.25 inches at the edge of the bladder (on top, bottom or both) and extend generally perpendicularly to, and away from, the body and down around the sides of the mattress. The thermally conductive strips may extend around to the bottom of the mattress such that they can transfer heat directly to the bed frame to aid with heat withdrawal from the bladder. As shown in FIG. 1A, patient 11 lies on top of the cooling pad 13, which may be under the mattress ticking or under a thin cushioning pad 17 in (FIG. 2A) such as foam, elastomer, or gel as well. This thin pad enhances patient comfort and reduces the "crinkling" sound that sometimes occurs with patient movement over the surface of the bladder 10. The thin pad results in a slightly reduced level of cooling and may not always be appropriate. The thin pad may include phase change and/or micro-encapsulated phase change materials to enhance thermal stability at the selected temperature. Conventional sheets and blankets may be used on the mattress, as desired.

In FIG. 1B conductive strips 12 extend around the top edge of the mattress and wrap around to the underside. FIG. 1B also shows an alternate bladder shape. Also shown in FIG. 1B is a pair of elevation pads 45 to lift the outer portions of the bladder relative to the central region, to aid gravitational feed to this central region. The elevation pads may be small foam pads placed under the bladder at the periphery thereof. An optional pair of powered cooling devices 46, such as Peltiers, is also attached to the outer conduction strips 12 to provide additional cooling, or to enhance cooling when ambient conditions are insufficient.

FIGS. 1C and 1D show additional embodiments of bladder shapes that reduce the area of occupant/cooling surface contact in the regions of the surface that do not need cooling. Typically, the bladder shapes correspond to the upper back, arms, and shoulders of the user. These bladder shapes are also intended to maximize bladder exposure to cooler ambient air at the periphery of the cooling surface. Central bladder 10 may be formed by joining two smaller bladders along a central seam 67 for ease of manufacturing. FIG. 1C. The essential functions of the device are not affected by the number of bladders, as long as pathways exist within the bladder(s) from the warm central zone 20 to the cooler peripheral zone 21. FIGS. 2A and 2B.

As indicated in FIGS. 2A and 2B, the substantially leakproof bladder 10 holds a refrigerant liquid 15, which may be hydrofluoroethane or other suitable refrigerant. The refrigerant preferably has a boiling point somewhat lower than average body temperature (37° C. or 98.6° F.) and greater than an average room temperature, or between about 23° C. (73.4° F.) and 35° C. (about 95° F.). Other refrigerants that may be used include pentafluoropropane, fluorochemical liquid, or a mixture thereof. A preferred refrigerant comprises from about 2 to 50 weight % of 1,1,1,3,3-pentafluoropropane, and from about 50 to 98 weight % of a fluorochemical liquid. The preferred refrigerant has a boiling point between about 80 and 94 degrees Fahrenheit, beyond which the liquid refrigerant 15 enters the gas phase 18. The refrigerant condenses at approximately the same temperature as it boils, i.e., between about 23° C. (73.4° F.) and 35° C. (about 95° F.).

As shown in FIGS. 2A and 2B, the entire cooling apparatus may be enclosed within a mattress ticking 16. Any suitable ticking material may be used, including nylon or urethanecoated fabric. The ticking 16 provides a cleanable surface that keeps moisture away from the inside of the support surface pad. In the embodiment shown in FIG. 2A, the cooling pad also includes a foam, elastomer, gel, or enclosed silicone fluid upper layer 17 under the ticking. The upper layer 17 (when present) lies on top of the bladder 10 for patient comfort.

After the refrigerant is placed in the bladder, sufficient space remains in the bladder 10 for expansion of the refrigerant liquid 15 as it enters the gas phase 18. When the user lies on the bed, the portion of the bladder 10 under the user's body is depressed by the body's weight, as shown in FIGS. 2A and 2B. This causes the liquid refrigerant to flow and collect in the central portion of the bladder that is directly beneath the occupant. The portions of the body exerting the highest pressure on the support surface are the portions most in need of skin cooling—i.e., the buttocks, low back, and torso. Therefore, with suitable choices of support materials, refrigerant will tend to collect in these regions to provide maximum cooling. As heat from the body is transferred downwardly into the support surface, the liquid refrigerant beneath the occupant is warmed to its boiling point. This heat is absorbed by phase change, as the liquid refrigerant enters the gas phase 18, and preventing additional warming, as long as liquid refrigerant 15 is present. The gas will then expand to fill the bladder space available to it, therefore expanding across the entire bladder and into the regions that overlay the periphery of the mattress.

FIG. 2B also shows two additional options. The elevation pads 45 are relatively firm foam pads placed under the outer portions of the bladder to raise the bladder relative to the central region. Small powered cooling devices, such as Peltiers 46, may be attached to the outer border of the conduction strips to aid cooling in extreme conditions. The powered cooling devices may be used for individuals who need or desire unusually high rates of cooling, or in conditions in which unpowered cooling is insufficient.

Once the gas refrigerant 18 has expanded to the cooler periphery of the mattress and condensed, liquid refrigerant 15 flows back to, and collects in, the lower, compressed central area within the bladder under the occupant. The refrigerant is available for continual cycles that are driven by the occupant's body heat, which drives the phase change and associated gas expansion, and by gravity, drives the liquid return flow. Importantly, the bladder shapes shown in FIGS. 1A, B, C and D have been found to be particularly effective, because they allow a high ratio of area in which heat is being exhausted to the environment ($A_{exhaust}$) to areas in which heat is being withdrawn from the body ($A_{absorbed}$), or $A_{exhaust}/A_{absorbed}$. Additionally, the additional area at the edges of the bladder is, in some embodiments, extended upwardly along the sides of the head so that this cooling region is continually exposed to room temperature air rather than the warmer environment under the arms and blankets immediately to the sides of the torso.

The bladder 10 is made of a durable, flexible, gas-impermeable material such as Tedlar or other material, so that it is comfortable to sit or lie on, and is strong enough to contain the refrigerant and withstand liquid 15 to gas 18 cycling over time. The bladder 10 is enclosed and sealed, so that the refrigerant does not escape. Even if the amount of refrigerant is found to decrease slightly over time in the bladder, the bladder can be periodically serviced and recharged by addition of refrigerant through a small valve. The bladder may be coated, more preferably by spraying or painting on a coating, with a visco-elastic material such as urethane. The viscoelastic coating produces more favorable mechanical characteristics, and deadens any crinkling sounds, which may occur when the occupant moves on the support surface pad 13). The coating also increases bladder durability.

In the interior of the hollow bladder 10, and substantially parallel to upper and lower surfaces 10a, 10b, respectively, of the bladder, is a compliant spacer mechanism 35, which is preferably a three-dimensional floating net, as shown in the cutaway portion in FIGS. 2A and 2B. The space net ensures that the bladder will not completely collapse when the occupant lies on the surface. There may be several layers of spacer netting material 35. Movement of liquid 15 and gas refrigerant 18 is therefore not restricted or blocked within the bladder 10 despite any wrinkling or compression due to occupant support. Distribution of the refrigerant in the bladder is enhanced by capillary action along the strands of the net or spacer mechanism. The preferred net is described in a previous application. Additionally, this spacer mechanism may have the surface converted with a radicalized species to optimize surface interaction with the refrigerant and enhance condensation, thereby increasing the efficiency of heat exchange.

As shown in FIGS. 1A, B, C, D, 2A and 2B, the conductive end portions of the support surface pad 13 include thermally conductive pathways 12 for conducting heat away from the central bladder and dissipating it. The conductive pathways are made of a highly thermally conductive material. The conductive material is preferred to have thermal conductivity greater than about 40 Watts/meter-degree Kelvin (40 W/m-K). Copper (~400 W/m-K), aluminum (~170 W/m-K), various carbon fibers or carbon fiber based fabrics, among other materials, may be used. The conductive pathways are preferably between about 0.0001 and 0.375 inch in thickness, depending on location and application. Sheets or strips of copper, aluminum, or a combination of copper and aluminum, are preferred, because they are thermally effective (i.e., high thermal conductivity), relatively inexpensive, and can easily be shaped to the appropriate configuration. They are also quite durable in thicknesses of 0.125 in., or greater and therefore, thicker strips may be used in specific regions of the bed. For example, the strips radiating from the central region may be thicker and more robust, because this is where the patient will be entering and exiting the bed, and resistance to deformation may be required.

In an alternate embodiment, the conductive pathways 12 are thicker where they connect to the bladder, thinning where they bend around the sides of the mattress and extend under the mattress 14. Although in some embodiments, thicker conductive pathways 12 do not wrap under the mattress, they are preferably long enough to wrap around and under the mattress 14. A pathway length of about 1 to 30 inches beyond the edge of the bladder is most preferred to give design flexibility for a range of thermal conditions and material properties. The conductive pathways that extend around the mattress and down may alternatively extend away from the mattress itself to reject heat directly into the cool ambient air beneath the bed.

An alternate embodiment is comprised of laminated thin sheets (each layer being several thousandths of an inch in thickness) of conductive pathway material. Also, the thin sheets 12 may be composed of different materials, such as copper and aluminum layers adhered to one another. The number of laminations may decrease with distance from the bladder to produce a conduction pathway that tapers from a relatively thick base to a thinner tip.

Since many hospital/nursing home beds have a top or bottom portion that can be raised and lowered, a solid metal sheet may not be comfortable or practical. Therefore a preferred embodiment herein includes a support surface pad 13 with conductive pathways 12 made of thin strips of copper, aluminum, silver, thermally conductive carbon fiber or polymer, combinations thereof, or any other highly thermally conductive and flexible material, as shown in FIGS. 1 through 14. The mechanical independence of these strips, particularly at the bed articulation region, allows for elevation of the head of the bed without interference of the conduction strips 12, which may be relatively rigid. Suitable conductive materials include sheeting, plate, or flashing composed of aluminum, copper, silver or other highly conductive material; copper or aluminum cable, or braided aluminum or copper, or conductive carbon fiber. The conductive strips 12 are glued, welded or otherwise attached together side by side, as shown in FIGS. 1 through 14 on top of the bladder, on the bottom, of the bladder, or both on top and on the bottom. Thermally conductive glues and greases are preferred due to their ability to enhance heat transfer between bladder wall and conduction strips.

In an alternative embodiment, the conductive strips 12 may be glued to a flexible, conductive strip support sheet 19 FIG. 4. The conductive strips 12 conduct the heat, and the flexible, non-conductive material 19 under/between the conductive strips allows the sides of the mattress 14 on which the support surface pad 13 is placed to flex when the head or foot portion of the bed is raised or lowered.

One end of each conductive strip 12 overlaps the lower bladder wall 10b at an end of the bladder. The upper faces of these end portions of the conductive strips 12 may be affixed to the outside of the lower bladder wall 10b using an appropriate binder, such as adhesive that bonds to metal. Heat conductive adhesive and/or heat conductive greases may enhance transfer of heat from the bladder 10 to the conductive strips 12. The lower faces of the remainder of the conductive strips 12 may be attached, such as by gluing or taping, to the flexible, conduction strip support sheet 19. Thermally enhanced glues, tapes and/or greases are not required for this attachment. Conductive strips 12 may also be glued to the top edges of the bladder 10b to withdraw maximum heat from the edges in order to keep the bladder as cool as possible.

FIG. 2A shows the separate layers of the device. Immediately beneath the patient 11 are the bed sheet and any other desired bedding materials, which are not shown. Between the patient and mattress is the ticking 16 although note that this entire cooling device 13 can also be used outside the ticking as an overlay. Beneath the ticking on the upper surface of the bedding is an optional thin cushioning pad 17 composed of compliant foam, elastomer, gel, or viscous fluid which may be confined in an envelope constructed of a thin, pliable material, which may be a urethane membrane. This cushioning pad may extend across the entire width of the mattress, or it may cover only the central portion of the mattress, leaving the outer edges of the bladder and conduction strips uncovered to enhance cooling of the periphery. FIG. 2B is a cross-sectional diagram of the mattress in use when no cushioning pad is used. Beneath the cushioning pad, when present, is the bladder comprising refrigerant, and the conventional construction materials of the mattress, which may be foam, gel, air cells, etc.

When a person sits or lies on a support surface, his or her body heat warms the support surface immediately under the body. Skin temperatures are greatest in the central regions of the body, such as the sacral area for a supine subject. Heat is conducted downwardly, and the refrigerant liquid 15 in the bladder 10 under the body is quickly heated by body heat to its boiling point. This area under the body may be referred to as the "warm zone" 20. The weight of the body on the soft mattress causes a depression of the reservoir that contains refrigerant relative to the edges of the support surface pad. The liquid refrigerant 15 converts to a gas 18 upon reaching the vaporization temperature of the refrigerant. The gas 18 expands to fill the bladder, and reaching the "cool zones" 21 on the periphery. The "cool zones" 21 here are the areas of the support surface that are not covered by the torso, and are generally the lateral areas of the support surface pad. As the vapor 18 expands toward the cool zone 21, it condenses and rejects heat at the periphery of the bladder. Heat is rejected in this region because: a) it is far from the heat source (the body); b) the area of the bladder at the periphery is relatively large, increasing the area for conductive, radiative, and convective heat transfer with the environment; c) Much of the "cool zone" area is configured toward the upper regions of the bed where the cool zone is exposed directly to room air, and is not exposed to the warming environment under the blankets, or contact with the arms, d) The conduction strips 12, which are attached to the edge of the bladder with thermally conductive adhesives, continue to draw heat from the edge of the bladder to still cooler regions at the sides, and, optionally, under the bed to the frame, further enhancing cooling area. These conduction strips increase cooling area significantly beyond the area of the bladder alone, because the bladder must not be wrapped downwardly around the edges and the bottom of the mattress or the condensing refrigerant will not return to the central warm region 20 of the support surface. As shown in the drawing figures, the device increases the area available for the flow of heat, without impeding the flow of condensed refrigerant. An alternative embodiment includes an active means of "pumping," or transporting the condensate by means other than gravity, to the heat zone.

Once cooled to the condensation point in the cool zone 21, the refrigerant liquid 15 then flows back to the warm zone 20 for additional cycles of heating and cooling. This has the effect of keeping the area under the body cool in an ongoing, steady state fashion. The bony prominences such as the sacrum and ischial tuberosities (where the risk of bed sores is severe) are the regions where the pressure on the surface is greatest so they will sink more deeply into the central zone have greater surface area in contact with the support surface pad 12 and therefore, are more exposed to the cooler temperature provided by the liquid refrigerant. The lack of body weight causes the cool zones to be elevated above the weighted warm zone. Gravity encourages the flow of the condensed refrigerant liquid 15 back to the warmest, lowest region, which is frequently along the centerline of the mattress/pad, where people typically are positioned. Support surface pads can be made for smaller, single bed mattresses, and for double, queen, and king size beds. In the latter case, the bladder will also easily accommodate several occupants lying side by side.

Use of the device can be customized for different patient/user needs. For example, a user whose lower back tends to sweat might use a support surface on his chair during work hours, or it could be used in conjunction with a car seat. In general, warmer areas of the body, such as the sacrum, trunk, and generally proximal regions, may require more cooling than cooler, distal regions of the body, such as the ankles and heels, which may require little or no cooling. The device described herein may be formed to any size and may be custom designed to suit tall or short people, small or large sized people, etc.

An alternate embodiment is shown in FIG. 3 (Top view) and FIG. 4 (Side view). This is a foam or gel mattress 22 that includes a small number (two to 10) of independent refrigerant-containing bladders 23. In this embodiment, several small bladders run essentially parallel to one another and are separated by 0.5 to 5.0 inches. Conductive strips 24 are attached to the edges of each of these bladders, as in the previously-described embodiments, and wrap downward around the edge of the mattress and may wrap under the bed. They may also flare (widen) or extend into the grooves 25 between bladders or connect to a single metal strip that runs along the edge of the mattress. In FIG. 4, note that grooves 25 that are 1.0 to 6.0 inches depth and 0.25 to 6.0 inches width have been cut in the mattress 22. The cooling bladders 23 rest on top of the foam pedestals 26 that separate these grooves. These grooves 25 have been found to help limit any perspiration that might build up over the bladders. Moisture wicks toward the ticking over the grooved regions, where evaporation is enhanced. Small moisture vapor vents 27 in the ticking may be present at one or both ends of each groove to ensure that any internal build-up of moisture is limited. Alternately, the independent bladders may rest atop a non-grooved mattress in a similar configuration.

An alternate embodiment suitable for use with a multiple air cell mattress 28 is shown in FIGS. 5, 5A (Top views) and FIGS. 6 and 6A (Side views). Either a static air surface, or a dynamic surface that changes the pressure in the air cells over time may be used. Independent bladders 23, constructed of a gas-impermeable material such as Tedlar or other material, rest atop each of the air cells 29 (FIGS. 5 and 6) or between the air cells 29 (FIGS. 5A and 6A) and are essentially parallel to one another. Conduction strips 30 are attached to the cooler peripheral zone of each bladder as described previously and wrap downward around the edge of the mattress. These conduction strips may flare or widen at the edge to enhance cooling, or they may connect to a single strip that runs along the edge of the mattress (62), most clearly shown in FIG. 6A.

An additional embodiment is shown in FIG. 7. This bladder configuration is suitable for either the grooved foam or gel mattress 22 shown in FIGS. 3 and 4 or the multiple air cell mattress 28 shown in FIGS. 5 and 6. In this configuration, multiple bladders form the cooling surface 31 and communicate with one another through a central chamber 32 or small number of interconnected tubes. The upper bladder (i.e., the bladder toward the head region of the bed) is much larger and flares markedly at the edge, extending upwardly toward the head of the bed to enhance cooling. The particulars of this embodiment are otherwise the same as those previously described.

FIG. 8 depicts an embodiment in which the heat exchange "cool zone" surface (63) is positioned outside the ticking 16, and suspended in the vertical plane or inclined at an angle at a level slightly above the support surface. In previously-described embodiments, the peripheral portions of the bladder, along with the attached conduction strips, are used to diffuse heat to the environment, but the entire bladder, including this peripheral heat exhaust zone, is inside the ticking. In the additional embodiment described here, the external heat diffusion surface is suspended such as from a head-board, IV pole, or equipment rack, and is either attached to the bed or positioned adjacent to it. The external heat diffusion surface comprises a flat bladder in contact with a sheet or plate of high conductivity material such as aluminum or copper. Ducts composed of gas-impermeable material such as Tedlar connect the cooling bladder to the external heat exchange diffusion surface, allowing for two-way communication of both vapor and condensed liquid refrigerant.

FIGS. 9 through 16, referred to earlier as "Conductive Devices", depict a series of cooling surface designs that that export the body's heat through the use of a highly thermally conductive support layer or series of layers. The simplest variation (FIG. 9) uses conductive fibers (47) as the primary elements of heat transport. In this embodiment, the fibers need not be embedded in a compliant cushion material, or encased in an envelope. Highly conductive forms of carbon fiber, such as pitch-based carbon fiber, in the filament, yarn, or fabric form may be used. These may also comprise other linear thermally conductive materials such as conductive polymers, filaments, wires, or filaments of copper or aluminum.

The quantity of conductive material and the specification for its use in this application is outlined in Tables 1 and 2 below.

TABLE 1

Specification for Conductive Material Quantity, Location, and Orientation

Preferred embodiments may be specified by the following constraints:

1) The top surface of conductive layer closest to the body must be within 2.0 inches (5.0 cm) of the body. That is, this layer or these layers may extend to several inches depth but the shallowest edge of the layer(s) must be within 2.0 inches of the occupant's body when compressed by the weight of the human body.
2) The conductive fibers must be oriented in such a way that they are oriented radially from, or nearly radially from, the body when viewed from above. For a mattress embodiment, this means the fibers are oriented parallel to the surface and perpendicular to the long axis of the body (47 in FIG. 9). In a seating application, the fibers run either transversely to the body along the seat or seat back, or they radiate from the region to be cooled (53, 54 in FIG. 14A).
3) There may also be a small number of fiber bundles oriented perpendicularly to the primary orientation of heat conduction described above. They will, when present, be oriented perpendicularly to the surface. These short, small bundles (64 in FIG. 9) may be concentrated in the region of maximum cooling requirement, and function to draw heat from the skin/support surface interface to deeper levels of the conductive layer(s) (47) to ensure efficient use of the entire conductive layer. Some fibers exhibit very non-uniform conduction characteristics. While they may conduct heat very efficiently along their length, conduction to adjacent parallel fibers is limited, such that deeper fibers will be under utilized without these central perpendicular bundles.
4) The primary conduction fibers may be laid between surface layers TABLE 1-continued Specification for Conductive Material Quantity, Location, and Orientation Preferred embodiments may be specified by the following constraints:

with no binding or carrier agent, or they can be bound with an elastic material such as "Sta-Put", a spray latex product, to stabilize the fibers and add additional strength with an elastic binding material. Other suitable binding agents include spray urethane, and elastic silicone glues (FIGS. 9, 9A and 10, 10A, 10B, 10C). Alternatively, the conductive fibers can be embedded in a cushion of gel, foam, elastomer or fluid, which may (FIGS. 13A, 13B, 13C, 13D) or may not (FIGS. 11 and 12A, 12B) be surrounded by a confining envelope. The conductive material may be enclosed in a compliant envelope without embedding this material in any additional cushioning material such as gel, foam, elastomer or fluid. In other words, the conductive material (generally fibers) may or may not be enclosed in a complaint envelope and may or may not be embedded in a cushioning material.

5) These fibers alternately may be incorporated into the ticking or seat cover, glued to the underside of the ticking or seat cover, glued or laid on the mattress underneath the ticking, or interleafed with layer or layers of mattress material such as foam.

6) The conductive layer, whether comprised of a cushioning material with embedded conductor, a cushioning material with embedded conductor that is surrounded by a fluid impervious envelope, conductive material enclosed in a compliant envelope, or essentially bare conductive fiber, must be compliant in the support regions such that it deforms significantly under the weight of the body. Quantitatively, this degree of mechanical compliance is defined as follows: If the conductive layer is placed on top of a standard foam hospital mattress, a standard 1.0 kg steel ball, when placed in the center of the support region, will cause the surface of the cushion to compress by greater than or equal to 0.25 mm.

7) The table below gives additional specificity with respect to the quantity of conductive material required to conductively transport heat sufficient to cool the typical body. The numbers represent the total layer thickness T of the conductive layer assuming the material is continuous with depth (i.e., a single layer), which is not required. For example, if the material has a conductivity of k = 300 W/m-K, a total conductive layer thickness T of between 0.01 and 10.0 cm is required. Alternatively, five sheets either adjacent to one another, or interspersed in surface material with this sum of thicknesses, or any combination of wires, filaments, or yarn to give the appropriate total thickness of conductive material may be used. The prepared Table 2 reflects constraints on the conductivity (k) of the material used in the transport layer and the thickness of this layer (T), such that k × T is greater than or equal to 0.03 W/K, and less than or equal to 30 W/K. For typical skin cooling applications of one to five degrees in room temperature settings with the geometries proposed here, k × T in the range of 0.5 to 8 W/K are optimal.

8) The mean conductivity of the cushion is greater than or equal to 8 W/m-K. This refers to the conductivity of the entire cushion, including the layer(s) of conductive material and any cushioning filler interspersed between these layers, in the direction of preferred heat transfer. The top of this layer is defined as the surface closest to the skin of conductive material (defined as greater than or equal to 8 W/m-K). The bottom of this layer is the surface of the cushion that is farthest from the skin, with this layer being having thermal conductivity greater than or equal to 8 W/m-K. Overall, this entire conductive layer, which may be comprised of several layers of varying thermal conductivities, has a mean conductivity of greater than or equal to 8 W/m-K in the direction of preferred heat transfer.

9) In some embodiments, the conductive layer is not continuous when viewed from above. (It will always be continuous in the direction of heat transfer, but the layer may be separated into parallel strips or bundles of conductive material.) For example, in one embodiment intended for use with an air cell mattress, the conductive material is positioned only between the air cells that run perpendicularly to the long axis of the mattress (i.e., side-to-side). In such cases, the k × T requirement is intended to apply to the mean thickness of conductive material across the region to be cooled. Sections of conductive material separated by a distance greater than 0.20 m when viewed from above, however, are to be treated as separate cooling cushions with respect to the k × T criterion.

The conductive layers will typically be positioned only in the central region of the bed to cool the low back, but may be positioned at any location on the bed, seat, or seat back surface to cool different regions of the body, or, in some cases, the entire body. For non-mattress applications such as office, residential, or vehicle seating, the specifications are essentially the same as for mattresses: the fibers will generally be oriented perpendicularly to the long axis of the body, but may be distributed across the entire seat cushion and seat back.

TABLE 2

Total Thickness of Conductive Material required for Given Conductivity k × T > 0.03 W/K and ≤30 W/K

| Conductivity (W/m-K) | Minimum Thickness T Required | | Maximum Thickness T Required | |
|---|---|---|---|---|
| | (m) | (cm) | (m) | (cm) |
| 40 | 0.000750 | 0.075 | 0.750 | 75.00 |
| 60 | 0.000500 | 0.050 | 0.500 | 50.00 |
| 80 | 0.000375 | 0.038 | 0.375 | 37.50 |
| 100 | 0.000300 | 0.030 | 0.300 | 30.00 |
| 125 | 0.000240 | 0.024 | 0.240 | 24.00 |
| 150 | 0.000200 | 0.020 | 0.200 | 20.00 |
| 200 | 0.000150 | 0.015 | 0.150 | 15.00 |
| 300 | 0.000100 | 0.010 | 0.100 | 10.00 |
| 500 | 0.000060 | 0.006 | 0.060 | 6.00 |
| 1000 | 0.000030 | 0.003 | 0.030 | 3.00 |
| 2000 | 0.000015 | 0.002 | 0.015 | 1.50 |
| 5000 | 0.000006 | 0.001 | 0.006 | 0.60 |
| 10000 | 0.000003 | 0.000 | 0.003 | 0.30 |

As shown in FIG. 9, the filaments lie across the mattress and conduct heat away from the body. This fiber orientation is critical, because conductivity is oriented disproportionately along the axis of the fibers or wires. To ensure that significant lateral conduction, i.e., parallel to the skin/support surface interface, occurs in the deeper levels of the fiber layer or layers, a small number of highly conductive fiber bundles (64) oriented perpendicular to the surface in the primary region of cooling in the center of the mattress or seat may be used. The conductive layer may simply be placed on top of (FIG. 10A), between layers of foam (FIG. 10B) or embedded in the foam mattress (FIG. 10C). Other particularly effective embodiments attach the fibers directly to the underside of the ticking or seat cover, or incorporate the fibers into the ticking itself (Top View, FIG. 16A, Side View FIG. 16B). In each of these "bare fiber configurations" (fibers not embedded in a protective cushion or envelope), the conductive layer is typically bound together and/or attached to an adjacent mattress layer using an elastomeric glue to enhance strength and absorb elastic deformation for the relatively brittle conductive fibers. Other embodiments allow these filaments to be placed on the surface of air cells of an air mattress. They may be formed in a continuous sheet or bundle, or concentrated intermittently, such as on the tops of series of air cells, or between the air cells.

Each configuration may be used inside the ticking, or outside the ticking, as a mattress or seating overlay.

FIG. 10A shows a cross-section of the conductive device positioned in the center of a mattress. The highly conductive fibers 47 run transversely to the long axis of the mattress, and are overlapping toward the edges of the support surface, with thermal diffuser sheets that run along the top of the periphery of the surface 48, down around the edge 49, or extend to the underside of the mattress 50. These diffuser sheets are composed of highly conductive material which we have defined as having thermal conductivity greater than or equal to 40 W/m-K in the direction of interest. Their function is to conduct heat from a broader I area, and to exhaust it to the cooler environment. The thickness of the diffuser sheets is from 0.0001 to 0.375. The diffuser sheets are preferred to be constructed of copper or aluminum, because these materials conduct well, are inexpensive, and mechanical compliance is not an issue for the diffuser.

FIG. 10B shows an embodiment in which the conductive layer is not continuous. In FIG. 10B, three conductive layers (47) are shown as separated by layers of less conductive but highly compliant mattress material (65), such as foam, gel, or elastomer. In FIG. 10C, the conductive layer is positioned beneath a thin cushioning layer (17) that may be penetrated by conductive fiber bundles (64) in the region of maximum cooling requirements.

FIG. 11 is a perspective view of a slightly different embodiment of the conductive cooling device in which the conductive fibers (47) are embedded in a thin cushion of elastomer, gel, or foam such as urethane or silicone (66). Again, the conductive bundles (64) that are perpendicular to the surface may be present in the region of maximum cooling requirements. Also shown are thermal diffuser strips, sheets, or plates that receive the heat from the warm zone and exhaust it to the cooler environment over a much broader surface area. These thermal diffuser strips may run along the edges on top of the mattress (i.e., in the same horizontal plane as the supine patient (48) and/or they may wrap around the edges of the mattress (49), and/or extend under the mattress.

The thermal diffuser regions are equivalent in function to that of a radiator in a typical heat transfer application. However, in many of the applications described in which the thermal diffuser is underneath a ticking and bedding, the bulk of the heat sinking from the diffuser is done not by radiation but conduction to the surface of the mattress ticking and bedding materials. Heat is released from this outer surface to the environment primarily by radiation and convection. For this reason, the term "thermal diffuser" is used, because it transports heat from the support surface to the environment by any of the possible modes of heat transfer, and not only by radiation.

TABLE 3

Specification of Constraints on Thermal Diffuser Materials and Geometry

1. The thermal diffuser regions are positioned at the distal regions of the support surface, away from the region to be cooled, such that heat conducted from the warm central region flows to this cooler diffuser area. The diffuser(s) may be along the top surface of the bed or seat, along the periphery, and/or it may extend to the sides of the surface, such as the edges of the bed or seat. They may also extend to the opposite side of the support surface (I.e., mattress, seat, or seat back), such that they extend underneath the bed, underneath a seat, or around to the back side of a seat back.
2. The thermal diffuser regions will be thermally connected to the thermal conduction layer of the support surface. That is, they may substantially overlap the conductive layer or, if there is 1.0 cm or more of material between the conductive layer and the thermal diffuser materials, this intermediate material will have thermal conductivity k > 8 W/m-K to ensure adequate flow of heat from warm regions to the diffuser. Typically, the thermal diffuser materials are partially embedded in the edge of the conductive layer, and extend substantially away from the conductive layer to increase the heat exhaustion area.
3. The thermal diffuser is constructed of material with high thermal conductivity (greater than or equal to 40 W/m-K). Some suitable materials for this purpose are aluminum (160-200 W/m-K), copper (400 W/m-K) or pitch-based carbon-fibers (50-1100 W/m-K and developing rapidly).
4. The thermal diffuser may comprise conductive strips, sheets, foils, louvers or fibers, yarn, or even fabric woven of conductive material. The diffuser may, in some applications, be enclosed in a thin (<0.25 inch) protective covering. For copper, aluminum, or other metals, the metal thickness must be 0.0001 to 0.375". For other materials the dimensions may be correspondingly varying, based on the properties. In some applications, the diffuser materials overlap a bed frame, metallic seat or vehicle structure to further enlarge the diffuser area.

TABLE 3-continued

Specification of Constraints on Thermal Diffuser Materials and Geometry

An extremely effective thermal diffuser for vehicle use draws heat from the seat surface to the outer surface of the vehicle where the moving fluid stream could remove tremendous quantities of heat when ambient temperatures are less than 85° F.
5. The surface area of the thermal diffuser may be variable, depending on the application because the amount of heat to be exhausted and the heat transfer conditions from the diffuser surface. In general, however, the surface area must be at least 0.25 times as great as the area of the body that is being cooled. Under typical heat transfer conditions for these applications, the diffuser area is 1.5 to 5.0 times the area of the region of the body to be cooled. In less favorable environments or when more cooling is required, the area may be 10 or more times the area of the body to be cooled.

FIGS. 12A and 12B are cross-sectional when viewed from the line shown in FIG. 11. FIG. 12A presents a version in use under the ticking. FIG. 12B shows the device over on top of the ticking. The conductive fibers (47) are embedded in a compliant cushion (66) of material that is comfortable to lie on. This embodiment may be constructed of soft elastomer, but may comprise gel, or foam or other soft material that will retain its form without an envelope. (That is, the fibers cannot simply be immersed in a viscous fluid in this non-enveloped embodiment.) Specifications for fiber quantity, depth of conductive layer, and orientation of fibers are as shown in Tables 1 and 2. The small conductive bundles (64) may be present in the region of maximum cooling, and oriented perpendicularly to the surface. Thermal diffuser strips may extend along the top surface (48), the edge of the mattress (49), and extend around to the underside of the mattress (50) in both the inside-ticking configuration (FIG. 12A) or the outside ticking version (FIG. 12B).

In FIG. 13A, an embodiment of the conductive cooling device is shown positioned in a cut-out groove or cavity found in the center of a foam mattress 41, and under the ticking, to provide cooling to the sacrum and lower back of a supine subject. FIGS. 13B, 13C and 13D are cross-sectional end-views along the section-line shown in FIG. 13A.

As shown in FIG. 13B, the entire device is enclosed in the mattress ticking 16. The top layer 41 is a cushioning pad that may simply be a foam pad or it may be the pliable membrane envelope that may contain gel, elastomer or fluid and perhaps, PCM.

The cushioning pad is positioned over a highly thermally conductive layer comprising of, from top to bottom, a pliable fluid and gel-impermeable envelope of membrane urethane or the like 43, an upper layer of highly conductive (>40 W/m-K) fabric such as woven carbon fiber 42, highly conductive particle or fiber, such as carbon fiber, conductive polymer, copper, aluminum, or silver coated aluminum dispersed or layered into a soft, pliable elastomer, gel, or viscous fluid such as urethane or silicone 44, a lower layer of conductive fabric 42, and a bottom impermeable membrane completing the envelope 43.

Alternatively in FIGS. 13B and 13C, the soft pliable elastomer, gel, or viscous fluid need not be present, such that the conductive material is enclosed in a compliant envelope without additional cushioning.

The conductive layer conducts heat from the central region to the cooler edge of the surface, so that heat does not build up to the extent that the skin temperature in this region approaches the typical thermally insulated temperature level of approximately 35° C. to 37° C. This conductive layer must be relatively pliable because it is underneath the occupant.

The conductive layer conducts heat toward the cooler edges, where it enjoins plates or sheets of conductive material that project inward 38. The conductive material will typically be constructed of Copper (conductivity=approx. 400 W/m-K) or Aluminum (conductivity=approx. 160-200 W/m-K depending on alloy). These projecting sheets or plates are intended to shorten the heat conduction path through the relatively expensive conduction layer 44. Because the inward-projecting conduction plates 38 are typically metal or copper, they are highly effective and efficient at transporting heat, and are relatively inexpensive. These plates assist with conduction to the side thermal diffuser plates 39 that extend down the outside of the mattress (but inside the ticking) and may extend fully around to the mid line of the mattress on the underside 40. A particularly effective thermal diffuser is so formed, because the area for heat transfer to the environment is very large, and much of the thermal diffuser is transferring heat to the coolest part of the room, which is under the bed. Additionally, the heat from the conduction plates under the mattress may be conducted directly through the thin ticking to the bed frame, which further amplifies the diffusion of heat.

Alternatively, the conductive layer itself may extend downwardly and around the edge of the surface, and wrapped onto the edges to form the thermal diffuser. This alternative may be more expensive than using a copper or aluminum thermal diffuser as described.

Heat travels from the occupant downward through the ticking 16 and the topper cushion pad 41. Heat conduction continues through the upper membrane of the envelope 43 and the conductive fabric 42, and into the conductive layer 44. As this conductive layer warms, heat is conducted to cooler adjacent regions. The cooler inwardly projecting conduction plates 38 provide an efficient path to the thermal diffuser plates 39 at the edges of the surface. Heat is transferred by convection from the diffuser surface to the ticking 16 by conduction, and to the surrounding environment by convection and radiation. Heat is also conducted through the diffuser plate itself to the underside of the bed, where these same transfers occur, in addition to conduction through the ticking to the frame, for further heat dissipation into the relatively constant ambient air of the hospital room, nursing home, office, or vehicle. The bed frame is part of the thermal circuit and serves as an additional thermal diffuser.

The inwardly projecting conductive sheets 38, when present, and the thermal diffuser plates 39 are preferred to be at least 0.0001" in thickness and composed of Copper or Aluminum (conductivity=approx. 160-200 W/m-K), in order to conduct the heat load presented by the central region of the typical human body across the thermal gradient that exists under actual use conditions. The thickness is dependent upon the number of sheets, the material used, the conductivity of the gel matrix that they project into, and the distance that they project toward the user.

FIG. 13C shows an embodiment in which the thermal diffuser plates 39 do not extend to the bottom of the mattress or seat, extending only along the vertical edge of the mattress 37. In FIG. 13D, an embodiment is depicted in which the layers of thermally conductive fabric 42 are not present. The bottom thermal diffuser plates 40 are also absent in this particular embodiment, although they could be present with or without the conductive fabric 42 layers. In some cases, the additional cushioning pad 41 may not be necessary, and without it, skin cooling will be more efficient. Configurations with little or no overlying cushion, therefore, provide the clinician with flexibility with respect to the trade-off between comfort (primarily, reducing skin interface pressure) and reducing skin temperature.

FIG. 14A is a front view of a seat intended for wheelchair, office, vehicle, or home use. The conductive material 53, 54 may be underneath the seat cover, incorporated into the seat cover, or placed over the seat or seat back as an overlay and again is oriented away from the body in a side-to-side or radial fashion. The conductive bundles 64 may be present in the warmest regions to aid with heat conduction perpendicular to the surface. The conductive material may be dispersed across the entire seat and seat back or it may be limited to specific regions that require cooling. Thermal diffuser sheets or strips 55, 56 are present on the seat back and seat.

FIG. 14B is a side view of the same seat showing the seat cover 52, conductive material 53, 54 on the seat back and seat. The thermal diffuser region wraps around the edge of the seat back and may extend behind section 55. The thermal diffuser 56 of the seat wraps down around the edges and may also extend underneath the seat.

FIGS. 15A and 15B are side views of an embodiment of a conductive cooling surface that is compatible with a typical air mattress. The conductive material 58 is shown running across the top of each transverse air cell in FIG. 15A. When viewed from above, this conductive material extends across the occupant support region of the mattress, and is oriented from side to side. The conductive material may be concentrated on top of the cells as shown, or it may be between the cells, as shown in FIG. 15B, or it may be continuously distributed in a layer across the top surface in the region in need of cooling.

FIGS. 16A and 16B are intended to show a case in which the conductive fibers are attached to or incorporated into the ticking. The conductive fibers may be laminated or woven into the ticking, or they may be attached to the ticking by means of an elastomeric adhesive that attaches and stabilizes the fibers, and also provides a measure of elastic strength to help the relatively brittle fibers withstand stresses. Additionally, the elastomeric adhesive or binder may provide some cushioning that enhances comfort. The concentration of conductive fibers 61 may be increased in regions that need additional cooling, such as the center of the mattress (or seat), or the fibers may be positioned in a relatively uniform manner. 16B is a side view showing the wrapping configuration of the conductive material around the edges, and perhaps to the underside of the ticking.

The device may use solid-to-liquid phase transition to limit skin warming and enhance thermal stability. A phase change material may be dispersed in a gel, elastomer, or fluid in a mixture (such as urethane or silicone) and contained in a pliable envelope, such as urethane film. Suitable phase change materials for use according to the invention include C16 to C19 alkanes (i.e., alkanes with between about 16 and 19 carbons), and mixtures thereof. Preferred alkanes are hexadecane (C16), heptadecane (C17), octadecane (C18), and nonadecane (C19). Alkanes may also be selected and mixed based on cost considerations, since some alkanes are relatively expensive. The alkanes used in this invention may be varied according to the degree of cooling desired for the particular part of the body that rests on that area of the support surface. Alkanes (or combinations thereof) may be selected according to the degree of cooling necessary to achieve the desired cooling effect.

The phase change material utilized may be varied according to cost, temperature requirements, and the length of time that cooling is desired. Preferably, the phase change materials melt at a temperature of between about 18° and 33° C., and more preferably, at a temperature between about 25° and 31° C. When a person sits or lies on a support surface, his or her body heat warms the support surface. Phase change materials cause the surface to resist warming, because the energy is absorbed by the PCM as it melts. Once the body's heat is conducted into the support surface from the skin, the thermal behavior departs from that of a conventional mattress because the heat that is conducted into the phase change material from the surrounding carrier is absorbed with no increase in temperature. This energy may be absorbed as latent heat in the phase change material's solid to liquid transition; that is, the energy melts a portion of the phase change material. As a result, the phase change material stays cooler at approximately the temperature of the phase transition, as does the surrounding carrier, envelope and skin.

Phase change materials are normally classified according to their melting points. Since most phase change materials have not been purified, they melt over a range of one or two degrees of temperature. When they are warmed to a temperature that is within this temperature range, the bulk of the phase change materials within the phase change material mixture melts and changes phase from a solid to a liquid. Many variables contribute to the performance of the support surface, including, but not limited to: 1) the type of phase change material and carrier; 2) whether the phase change material is encapsulated; 3) the ambient temperature; 4) the rate at which heat is transported from the region directly under the occupant to the edges of the support surface; 5) the size and body temperature of the particular occupant laying or sitting on the support surface; and 6) how long the occupant has been laying or sitting on the support surface. The phase change temperature, or melting point, of the phase change material distributed in the support surface is selected so that it is a few degrees cooler than the temperature that is imparted to the body, because the PCM must remain cooler than the skin surface in order to draw heat from the skin.

The caregiver need not be concerned that the product will be so cold that it will harm the occupant. The melting point, as a physical property of the phase change material, is quite specific and extremely consistent. The type of phase change material and the number and type of layers beneath are selected to ensure that the temperature that reaches the skin is one that is not harmful, and in fact is known to convey a therapeutic benefit.

The phase change material, when present, is preferably microencapsulated so that it remains evenly distributed throughout the carrier even after repeated cycles of cooling and warming. The distribution of the phase change material into small, generally spherical capsules with a diameter of between about one and 100 microns significantly enhances heat transfer between the surrounding medium and the phase change material. Microencapsulation also prevents interaction, chemical or otherwise, over time between the phase change material and the carrier, or envelope, material, thus increasing product longevity. This structure also ensures pad conformability, which would not be the case if the pad were composed of pure alkane, which physically resembles candle wax, in the solid state. Any suitable method for encapsulating the phase change material in a protective coating can be utilized. In one embodiment, powdered phase change material is used, because it enhances heat transfer due to its higher surface area.

The phase change materials are preferably microencapsulated in a thin coating, which is preferably a polymer. The coating preferably forms a generally spherical shell around the phase change material with a shell thickness of between about 0.003 and 2.0 microns, and more preferably between about 0.03 and about 0.05 microns thick.

From the foregoing it can be realized that the described devices of the present inventions may be easily and conveniently utilized as a therapeutic support surface, such as a mattress, mattress overlay, a wheel chair cushion, seat cushion or seat back or seat overlay for home, office, or vehicle applications. It is to be understood that any dimensions given herein are illustrative, and are not meant to be limiting.

While preferred embodiments of the invention have been described using specific terms, this description is for illustrative purposes only. It will be apparent to those of ordinary skill in the art that various modifications, substitutions, omissions, and changes may be made without departing from the spirit or scope of the invention, and that such are intended to be within the scope of the present invention as defined by the following claims. It is intended that the doctrine of equivalents be relied upon to determine the fair scope of these claims in connection with any other person's product which fall outside the literal wording of these claims, but which in reality do not materially depart from this invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

BRIEF LIST OF REFERENCE NUMBERS USED IN THE DRAWINGS

10. Bladder or of skin cooling surface containing refrigerant liquid and gas (10a: upper bladder membrane; 10b: lower bladder membrane)
11. Patient on top of cooling surface
12. Conduction strips or "conductive pathways" that overlap edge of bladder and extend outward and own around edge of mattress and may extend beneath mattress
13. Skin cooling surface pad
14. Conventional mattress that cooling pad may be built into, inserted into, or placed upon
15. Refrigerant in Bladder (in Liquid phase)
16. Ticking surrounding mattress
17. Thin foam, gel, elastomer, or envelope containing viscous fluid to enhance occupant comfort and reduce interface pressure on occupant's skin. (May include PCM)
18. Refrigerant in Bladder (in Gas phase)
19. Conduction strip support sheet
20. Warm central zone of bladder where heat is absorbed in Gas Expansion Device
21. Cooler peripheral zones of bladder where heat is exhausted in Gas Expansion Device
22. Gel or foam mattress that may be grooved
23. Small, Independent bladders containing refrigerant in multi-bladder Gas Expansion Device
24. Conductive strips that overlap edge of independent bladders
25. Grooves in mattress
26. Mattress pedestals between grooves
27. Moisture vapor vents in ticking
28. Multiple air cell mattress (static or pressure-varying with time)
29. Air cells of multiple air cell mattress.
30. Conduction strips
31. Multiple communicating bladder configuration
32. Central communication chamber between bladders
33. Flaring upper bladder to enhance cooling
34. Heat Exchanger (optional)
35. Spacer mechanism or space net
36. Vertical or inclined plane Heat Exchanger outside of mattress ticking 37. Gas Impermeable conduits connecting bladder with Vertical or Inclined Heat Exchanger
38. Inward projecting conductive sheeting or plates (or conduction path-shorteners)
39. Side Thermal Diffuser plate
40. (Optional) bottom Thermal Diffuser plate
41. (Optional) topper cushioning pad for occupant comfort (may include PCM)
42. Highly thermally conductive fabric
43. Impermeable envelope contain conductive gel
44. Thermally conductive gel, elastomer, or fluid
45. Elevation pad to lift outer portions of refrigerant-containing bladders slightly relative to central portions
46. (Optional) powered cooling device such as Peltier to enhance cooling under extreme conditions
47. Highly conductive fibers oriented transverse to the mattress and perpendicular to the border of the body
48. Thermal Diffuser sheets adjacent to fibers to enlarge heat exhaust region along top edge
49. Thermal Diffuser sheets adjacent to fibers to enlarge heat exhaust region by conducting heat down and along side (edge)
50. Thermal Diffuser sheets adjacent to fibers to enlarge heat exhaust region by conducting heat down and extending underneath mattress
51. Highly conductive fiber layer extends to edge, side, and underneath mattress to function as thermal diffuser without need for additional thermal diffuser materials
52. Seat Covering
53. Transverse or radially directed highly conductive fibers on seat back
54. Transverse or radially directed highly conductive fibers on seat
55. Thermal diffuser sheets wrapping along seat back edge and behind seat back
56. Thermal diffuser sheets wrapping along side of seat and underneath
57. Ticking over air cell mattress
58. Transversely oriented highly conductive fibers on top of, between air cells, or continuously configured in a cooling layer on air mattress
59. Thermal diffuser sheets along side of mattress and may extend beneath or along top edges of mattress
60. Air cells of air mattress
61. Highly conductive fibers attached to or incorporated into the ticking or seat cover.
62. Thermal Diffuser edge cooling strip or sheet.
63. Heat Exchange "Cool Zone" exhaust surface outside ticking
64. Conductive fiber bundles perpendicular to surface in warm region to conduct heat to deeper transverse conductive layers
65. Foam, Gel, or Elastomer cushioning layers between conductive layers
66. Cushion of foam, gel, or elastomer in which conductive fibers or filaments are embedded in prescribed quantities, depth, and orientations.
67. Seam joining two bladders into two-bladder configuration.
68. Conduction Device

What is claimed is:
1. A thermally conductive support surface for a human, comprising:
 a) a thermally conductive cushion comprising a plurality of thermally conductive fibers; and
 b) a thermal diffuser that communicates with said thermally conductive fibers, wherein thermal conductivity of said thermally conductive cushion is greater than eight (8) watts per meter-degree Kelvin.
2. A thermally conductive support surface for a human as described in claim 1, wherein said thermally conductive cushion is centrally disposed within said support surface, and said thermal diffuser is present on a periphery of said support surface.
3. A thermally conductive support surface for a human described in claim 1, wherein said thermal diffuser comprises metal.
4. A thermally conductive support surface for a human as described in claim 1, further comprising a mattress, and wherein said thermally conductive cushion is centrally disposed on said mattress, and said thermal diffuser is present on a periphery of said mattress.
5. A thermally conductive support surface for a human as described in claim 1, wherein said plurality of thermally conductive fibers extend beyond a side of said thermally conductive cushion and communicate with said thermal diffuser.
6. A thermally conductive support surface for a human as described in claim 5, wherein said plurality of thermally conductive fibers that extend beyond a side of said thermally conductive cushion extend perpendicularly away from a longitudinal axis of said thermally conductive cushion, and wherein said plurality of thermally conductive fibers communicate with said thermal diffuser.
7. A thermally conductive support surface for a human as described in claim 1, wherein said plurality of thermally conductive fibers extend vertically downward from a top surface of said thermally conductive cushion.
8. A thermally conductive support surface for a human as described in claim 1, wherein said plurality of thermally conductive fibers comprises bundles of individual thermally conductive fibers.
9. A thermally conductive support surface for a human as described in claim 1, wherein at least a portion of said diffuser is remote from said thermally conductive cushion.
10. A thermally conductive support surface for a human as described in claim 1, wherein said plurality of thermally conductive fibers has thermal conductivity of greater than eight (8) watts per meter-degree Kelvin.
11. A thermally conductive support surface for a human, comprising:
 a) a thermally conductive cushion comprising a plurality of thermally conductive fibers; and
 b) a thermal diffuser that communicates with said thermally conductive fibers, wherein thermal conductivity for said thermally conductive cushion is a function of thickness of said thermally conductive cushion according to the following table:

| Conductivity | Minimum Thickness T Required | | Maximum Thickness T Required | |
| --- | --- | --- | --- | --- |
| (W/m-K) | (m) | (cm) | (m) | (cm) |
| 40 | 0.000750 | 0.075 | 0.750 | 75.00 |
| 60 | 0.000500 | 0.050 | 0.500 | 50.00 |
| 80 | 0.000375 | 0.038 | 0.375 | 37.50 |
| 100 | 0.000300 | 0.030 | 0.300 | 30.00 |
| 125 | 0.000240 | 0.024 | 0.240 | 24.00 |
| 150 | 0.000200 | 0.020 | 0.200 | 20.00 |
| 200 | 0.000150 | 0.015 | 0.150 | 15.00 |
| 300 | 0.000100 | 0.010 | 0.100 | 10.00 |
| 500 | 0.000060 | 0.006 | 0.060 | 6.00 |

-continued

| Conductivity | Minimum Thickness T Required | | Maximum Thickness T Required | |
|---|---|---|---|---|
| (W/m-K) | (m) | (cm) | (m) | (cm) |
| 1000 | 0.000030 | 0.003 | 0.030 | 3.00 |
| 2000 | 0.000015 | 0.002 | 0.015 | 1.50 |
| 5000 | 0.000006 | 0.001 | 0.006 | 0.60 |
| 10000 | 0.000003 | 0.000 | 0.003 | 0.30. |

12. A thermally conductive support surface for a human, comprising:
  a) a bladder comprising a pocket within a proximal portion of said bladder, said bladder comprising a distal region that is remote from said pocket;
  b) a refrigerant that is contained within said bladder, wherein said refrigerant has a boiling point that is not greater than 36 degrees Celsius, wherein a portion of said refrigerant that is in a liquid form collects in said pocket, and wherein body heat is transferred to said liquid, whereupon a portion of said liquid vaporizes and transfers to said distal region;
  c) a plurality of thermally conductive fibers disposed between a thermally conductive diffuser and said distal region of said bladder, wherein the plurality of thermally conductive fibers thermally communicate with said distal region and transfer heat from said refrigerant in said distal region to said thermally conductive diffuser that is positioned remotely from the bladder.

13. A thermally conductive support surface for a human as described in claim 12, wherein said bladder comprises two compartments, wherein each compartment does not permit transfer of refrigerant to a remaining compartment, and wherein each compartment comprises a pocket and a distal region, and comprising a first plurality of thermally conductive fibers that thermally communicate with a first of the two compartments, and comprising a second plurality of thermally conductive fibers that thermally communicate with a second of the two compartments.

14. A thermally conductive support surface for a human as described in claim 12, wherein the total area of the diffuser is not less than 0.25 times as large as the surface area of a heat source that contributes said body heat to said refrigerant.

15. A thermally conductive support surface for a human as described in claim 12, wherein the resulting support surface comprises a plurality of thermally conductive fibers in a central support area of the thermally conductive support surface that is occupied by a user and the plurality of thermally conductive fibers conduct a user's body heat.

16. A thermally conductive support surface for a human as described in claim 12, wherein a plurality of thermally conductive fibers extend across a central support area of the thermally conductive support surface that is occupied by a user and the plurality of thermally conductive fibers conduct the user's body heat to a periphery of the thermally conductive support surface.

17. A thermally conductive support surface for a human as described in claim 12, wherein the refrigerant is not transported within said bladder by a pump.

18. A thermally conductive support surface for a human as described in claim 1, further comprising a thermoelectric module, wherein said thermoelectric module removes heat from said thermally conductive diffuser.

19. A thermally conductive support surface for a human as described in claim 12, further comprising a thermoelectric module, wherein said thermoelectric module removes heat from said thermally conductive diffuser.

20. A thermally conductive support surface for a human as described in claim 1, wherein said cushion comprises an envelope and wherein a portion of said thermally conductive fibers are contained within said envelope.

* * * * *